United States Patent
Posnett

(10) Patent No.: US 6,664,042 B1
(45) Date of Patent: Dec. 16, 2003

(54) DETERMINING VIRAL LOAD IN DOUBLE NEGATIVE T CELLS

(75) Inventor: David N. Posnett, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

(21) Appl. No.: 09/890,010

(22) PCT Filed: Jan. 26, 2000

(86) PCT No.: PCT/US00/01959
§ 371 (c)(1),
(2), (4) Date: Nov. 23, 2001

(87) PCT Pub. No.: WO00/43551
PCT Pub. Date: Jul. 27, 2000

Related U.S. Application Data

(60) Provisional application No. 60/117,447, filed on Jan. 26, 1999.

(51) Int. Cl.[7] .................................................. C12Q 1/70
(52) U.S. Cl. ................ 435/5; 435/6; 435/7.1; 435/7.24; 435/7.9; 435/7.92; 435/974; 435/975; 436/518; 436/536; 530/388.73; 530/388.75
(58) Field of Search ................ 435/5, 6, 7.1, 7.24, 435/7.9, 7.92, 974, 975; 436/518, 536; 530/388.73, 388.75

(56) References Cited

U.S. PATENT DOCUMENTS 5,420,264 A * 5/1995 Seed et al. .................. 536/23.5

FOREIGN PATENT DOCUMENTS

EP 0 230 768 A1 * 5/1987

OTHER PUBLICATIONS

McSharry et al. "Detection and quantitation of human immunodeficiency virus–infected peripheral blood momonuclear cells by flow cytometry", J. of Clinical Microbiology, vol. 28, No. 4(Apr. 1990). QR46.J87.*

Patterson et al. "Detection of HIV–1 DNA and messenger RNA in individual cells by PCR–driven in situ hybridization and flow cytometry", Science, vol. 260(1993).*

* cited by examiner

*Primary Examiner*—Jeffrey Stucker
(74) *Attorney, Agent, or Firm*—Nixon Peabody LLP

(57) ABSTRACT

The present invention provides a method for determining viral load in a patient infected with human immunodeficiency virus, which is useful in patients where viral loads are not detectable in plasma. The levels of human immunodeficiency virus are measured in $CD4^-CD8^-$ double negative cells. Furthermore, the invention also provides a kit for determining viral load in a patient infected with human immunodeficiency virus.

31 Claims, 14 Drawing Sheets

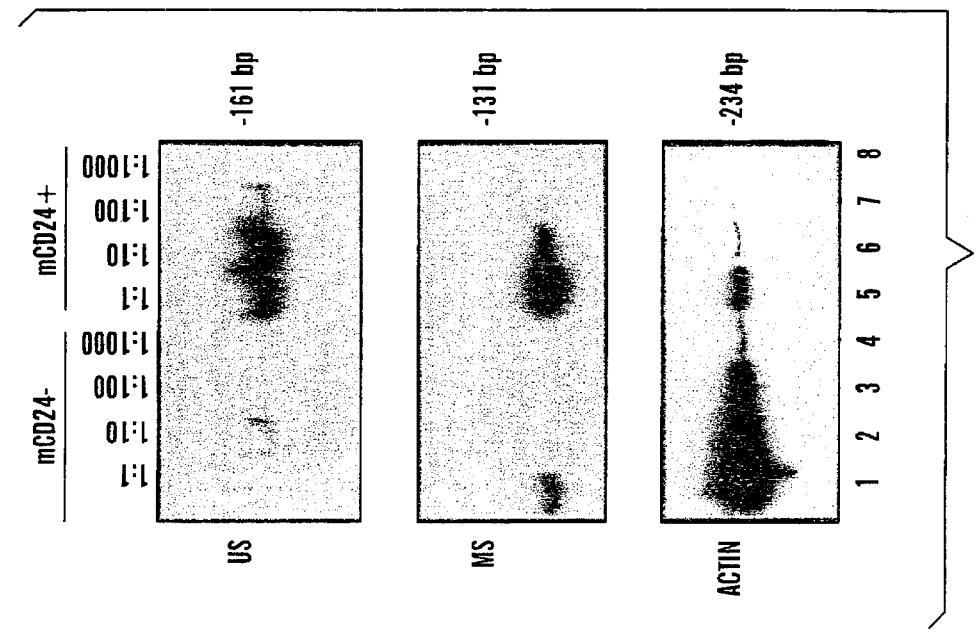
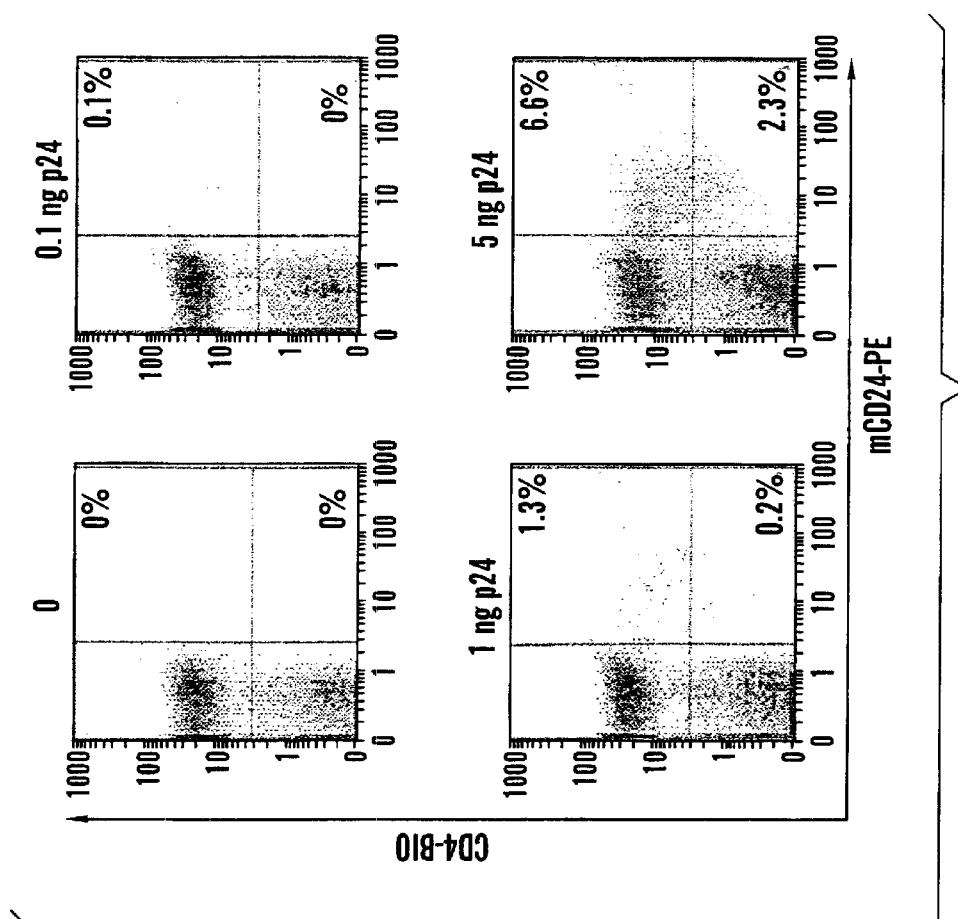
FIG. 3A
FIG. 3B

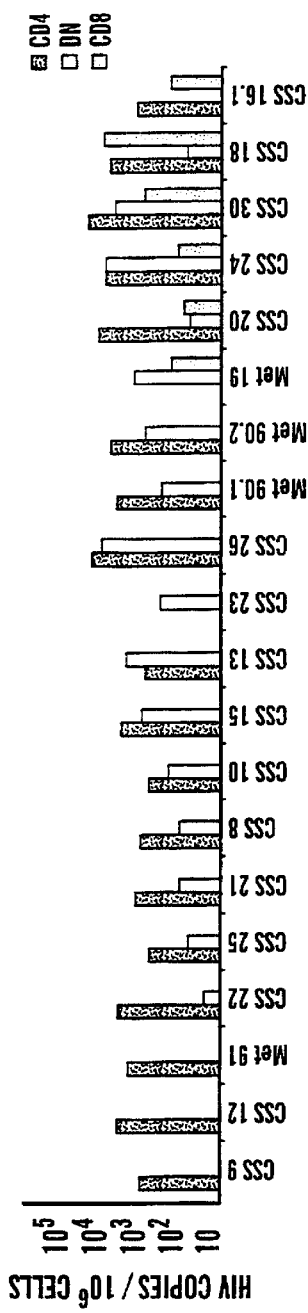
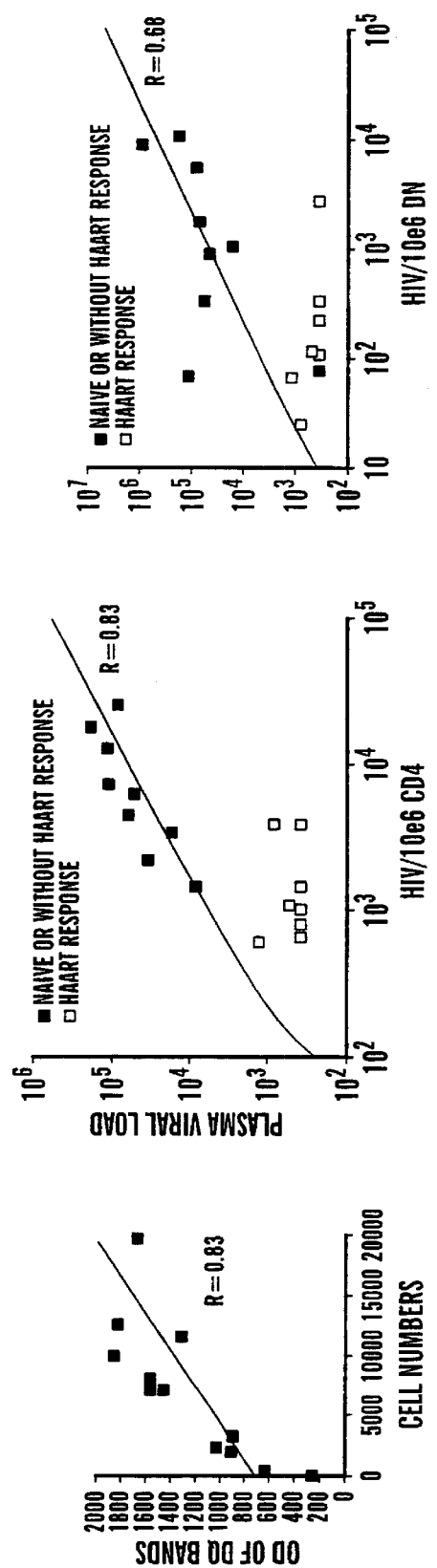

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

```
<400> SEQUENCE: 1
cctcatgaag atcctcaccg                                                        20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 2
aaggaaggct ggaagagtgc                                                        20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:  Primer

<400> SEQUENCE: 3
tggacatgca ctgtcttgc                                                         19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 4
ggtgatccaa gacttggagg                                                        20
```

DETERMINING VIRAL LOAD IN DOUBLE NEGATIVE T CELLS

The present application is the National Stage of PCT/US00/01959 which claims the benefit of U.S. Provisional Patent Application Ser. No. 60/117,447, filed Jan. 26, 1999.

The subject matter of this application was made with support from the United States Government under Grant No. R01 AI 22333 from the National Institutes of Health. The United States Government may retain certain rights.

BACKGROUND OF THE INVENTION

The type-1 human immunodeficiency virus (HIV-1) has been implicated as the primary cause of the slowly degenerate disease of the immune system termed acquired immune deficiency syndrome (AIDS). Infection of the CD4+subclass of T-lymphocytes with the HIV-1 virus leads to depletion of this essential lymphocyte subclass which inevitably leads to opportunistic infections, neurological disease, neoplastic growth and eventually death. HIV-1 infection and HIV-1 associated diseases represent a major health problem and considerable attention is currently being directed towards the successful design of effective therapeutics.

Like other retroviruses, HIV down-regulates its own receptor (51, 52). CD4 down-regulation may alter signaling pathways because of the association of CD4 with $p56^{lck}$ (53), protect from glycoprotein (gp120)-induced apoptosis (53), or prevent superinfection (54). However, evidence for CD4 down-regulation in HIV-positive subjects is still lacking and most prior work was performed with transformed cell lines with unknown relevance in vivo. CD4 down-regulation occurs in primary human peripheral blood lymphocytes (PBL) infected with a reporter virus (27, 55). For example, in PBL infected with HIV-HAS (HIV with a murine heat stable antigen reporter gene), $HSA^+$ cells progressively lost CD4 expression, while maintaining high levels of CD4 mRNA and unaltered levels of T cell receptor (TCR) and CD8 expression (57). Therefore, infected double-negative (DN) T cells are generated from $CD4^+$ precursors. In normal subjects, DN cells are a heterogeneous population. They include natural killer T cells implicated in initiation of a T helper-2 response (56). Whether such normal DN subsets can become HIV infected is not known.

In earlier ex vivo studies, HIV DNA seemed to be exclusively in the $CD4^+$ population of peripheral T lymphocytes (57, 58). It is known now that $CD8^+$ cells can also be infected (59, 60), but there are no data on DN T cells obtained ex vivo.

In the past few years, a number of drugs, including protease inhibitors, have been developed which greatly decrease the viral load of HIV in infected patients. The discovery of these various drugs has led to cocktail therapies such as the successful highly active antiretroviral therapy (HAART). Current medical cocktails are so potent that the viral load becomes "undetectable" in treated patients using standard viral load tests (usually with a lower limit of detection between 25–400 virions/ml of plasma). Even though the viral load may be non-detectable in plasma, discontinuing therapy leads to a resurgence of the infection. Therefore, HIV drug therapy must be maintained indefinitely. Thus a need exists for an improved method of detecting HIV in patients. Furthermore, current tests do not distinguish functional (infectious) virus from inactivated or non-infectious virus. Thus, there is a need for a method which preferentially identifies viable HIV virus in patients.

SUMMARY OF THE INVENTION

The present invention provides a method for determining viral load in a patient infected with human immunodeficiency virus. The levels of human immunodeficiency virus are measured in $CD4^-$ $CD8^-$ double negative cells.

The invention also provides a kit for determining viral load in a patient infected with human immunodeficiency virus. The kit contains a component for separating T cells from a biological sample; a component for separating $CD4^-$ $CD8^-$ cells from $CD4^+$ or $CD8^+$ cells; and a component for detecting human immunodeficiency virus.

BRIEF DESCRIPTION OF THE DRAWINGS

FIG. 3A shows the infection of activated normal human PBL with HIV-HSA. $2\times10^6$ T cells were infected with the indicated amounts of HIV-HSA and cultured for 8 days as described in Materials and Methods. Cells were then stained with biotinylated anti-CD4-bio and anti-mCD24-PE mAb. FIG. 3(B) shows the RT-PCR for un-spliced (US) and multi-spliced (MS) HIV RNA. $mCD24^+$ HIV-HSA infected PBL were sorted with magnetic beads eight days after infection as described in Material and Methods. There were fifty-fold more $mCD24$ than $mCD24+$cells prior to sorting and cDNA was prepared from the total sorted subset. Ten-fold serial dilutions of cDNA from $mCD24^-$ (lanes 1 to 4) and $mCD24^+$ (lanes 5 to 8) samples were amplified by radioactive RT-PCR using primers specific for US. MS HIV cDNA or for actin mRNA. The size of each PCR product in base pairs and the dilution of the cDNA used is indicated. Films were exposed for 16 hours.

FIG. 6 shows annexinV staining of primary lymphocytes infected with HIV-HSA.

FIG. 10B provides an estimate of HIV gag copy numbers in each sorted cell subset and quantification of the band intensities (see FIG. 10A). The estimated gag copy numbers were corrected by cell numbers, as measured with the FACSvantage counters at the end of each sort. FIG. 10C shows the correlation between cell number equivalents used for PCR and intensity of HLA-DQα PCR bands. Band intensities of cellular DQα PCRs correlated well with cell number equivalents determined by the FACS counter at the end of each sort. A good correlation was obtained with samples derived from sorted DN subsets of HIV-positive patients (similar results were obtained with sorted CD4 subsets). This result rules out variable efficiencies of DNA isolation and PCR amplification and indicates that the chosen range of cell number equivalents (<20,000 DN cells) allows quantitative assessment of cellular DNAs, such as HLA DQα. It also shows that HIV gag copy number can be calculated as a function of cell number (see FIG. 10B). FIG. 10D shows the correlation between plasma viral load and CD4 cellular viral load indicates that there is a variable viral load in CD4 cells in HAART-treated patients who have no detectable plasma viral load. FIG. 10E shows the correlation between plasma viral load and DN cellular viral load indicates that there is a variable viral load in DN T cells in HAART-treated patients who have no detectable plasma viral load. Undetectable plasma viral loads were assigned a value of 400 RNA copies per ml, i.e., the limit of detection of the clinical test used.

FIG. 11 shows the HIV DNA in T cell subsets from LN.

DETAILED DESCRIPTION OF THE INVENTION

Figure 1:
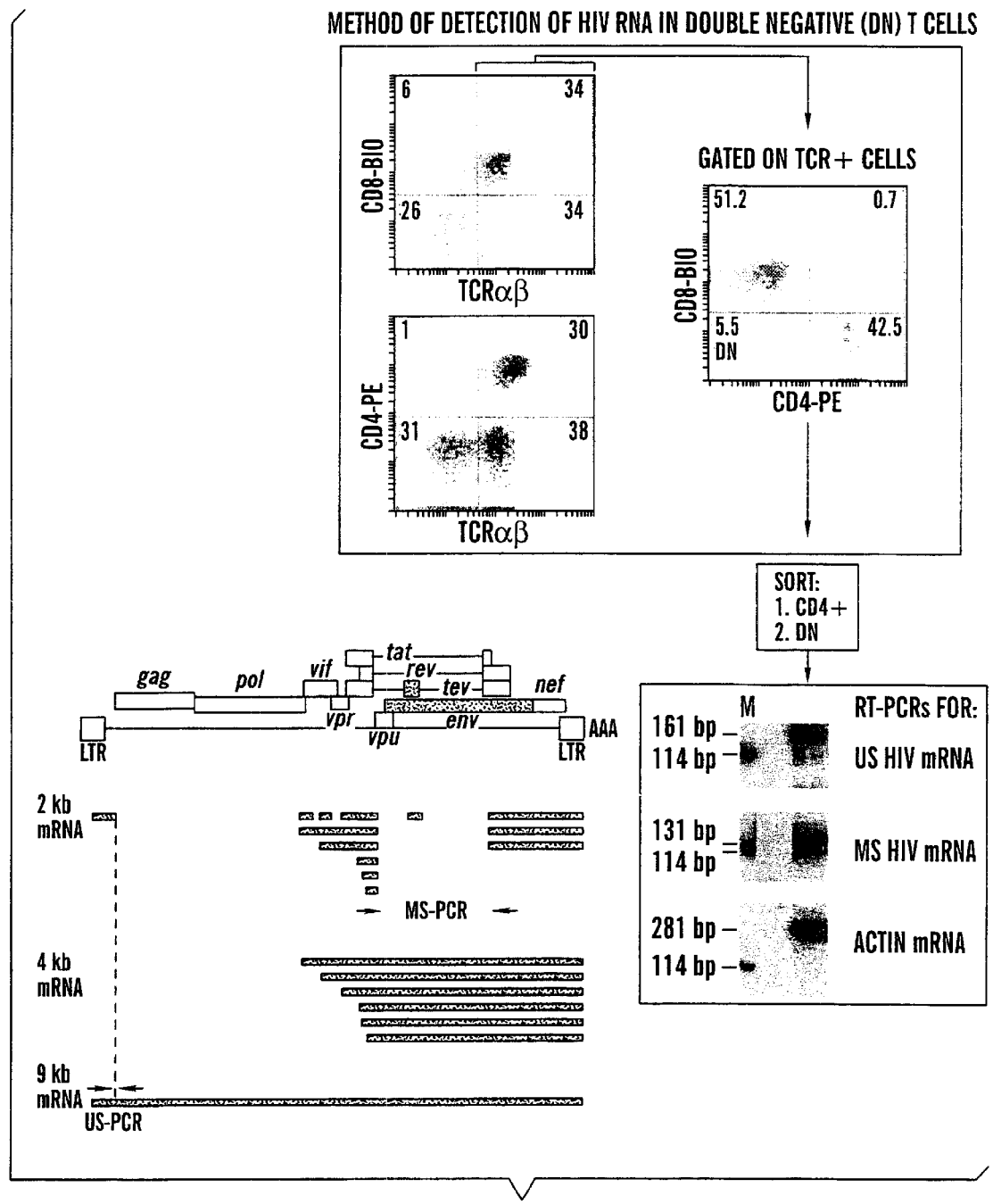
FIG. 1 schematically depicts a method for detection of HIV in double negative T cells. The upper box shows the cytometry histograms of stained peripheral blood mononuclear cells from an $HIV^+$ patient. T cells which are $TCR\alpha\beta$ positive are further subdivided into a $CD8^+$ fraction, a $CD4^+$ fraction, and a double negative ("DN") fraction, which in this case measures 5.5% of all T cells. The double negative and the $CD4^+$ cells are then sorted with magnetic beads. The lower box shows RT-PCR results with easily detectable US and MS HIV RNA, where as the inset on the lower left shows the location of the PCR primers that were used for the MS and US PCRS.

The present invention provides a method for determining viral load in a patient infected with human immunodeficiency virus. In particular the present method is useful for detecting HIV viral load in patients with low viral loads. Patients being treated with cocktail therapies may have viral loads which are so low as to be non-detectable using standard procedures. However, this undetectable virus can re-infect the patient upon cessation of therapy.

The present method entails measuring the levels of human immunodeficiency virus in CD4⁻ CD8⁻ T cells. As discussed in more detail below, infectious HIV will lead T cells to develop into CD4⁻ CD8⁻ cells. The lack of CD4 and CD8 can be used to identify those cells which contain active HIV.

The present method can be carried out by first isolating T cells from a patient sample. The CD4⁻ CD8⁻ cells are then isolated. This may be accomplished by removing the CD4⁺ and CD8⁺ cells. The level of human immunodeficiency virus is then determined in the isolated CD4⁻ CD8⁻ T cells.

Isolating the T cells may be accomplished by a wide variety of means. In a preferred embodiment, T cells are isolated by virtue of a T cell specific marker. Antibodies or other ligands which bind to the T cell specific marker can be used to remove T cells from the sample. This can be done by adhering the antibodies or ligands to magnetic beads, a column matrix, a filter, microtiter plates, or other solid support. Standard immunological procedures can be used to bind to and purify the T cells. In a preferred embodiment, magnetic beads coated with antibodies specific for a T cell specific marker is used to isolate T cells.

The T cell specific marker can be any protein, lipid, or cell structure which is found on T cells, but not on other plasma cells. Preferred T cell specific markers are $CD2^+$, $CD3^+$, and T cell receptor $\alpha\beta$. The most preferred T cell specific marker is $CD3^+$.

In a preferred embodiment, the isolation of the CD4⁻ and CD8⁻ T cells is carried out by removing CD4⁺ and CD8⁺ T cells from the patient sample.

The levels of human immunodeficiency virus may be determined by measuring levels of human immunodeficiency virus DNA, human immunodeficiency virus RNA, or human immunodeficiency virus proteins.

In one embodiment of the invention, the levels of human immunodeficiency virus is determined by measuring levels of human immunodeficiency virus DNA. The quantity of DNA may be determined using sequence specific hybridization. The terms "hybridization" and "hybridizing" refers to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

The hybridizing probes may be labeled with a radioactive marker, a fluorescent marker, or a chemical marker. Branched DNA (bDNA), involves oligonucleotides with branched structures that allow each individual oligonucleotide to carry 35 to 40 labels (e.g., alkaline phosphatase enzymes) (78). These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Stringency as it is commonly used in the art (79–80). For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 mu g/ml denatured salmon sperm DNA (ssDNA). In a most preferred embodiment, hybridization will occur at 42° C. in 250 mM NaCl, 25 mM trisodium citrate, 1% SDS, 50% formamide, and 200 mu g/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Although hybridization may be carried out using any portion of the HIV genome, some portions of the genome may be preferred because they are more conserved among isolates of HIV than other regions. In particular, the gag and pol genes are preferred as conserved segments of the HIV genome. However, other parts of the genome may be selected due to the higher variability in those sequences, if one desires to discriminate between different isolates.

In a preferred embodiment of the invention, the RNA or DNA in the sample will be amplified by polymerase chain reaction ("PCR") prior to analysis to increase the sensitivity (81).

In an alternative embodiment, the level of human immunodeficiency virus may be determined by measuring levels of human immunodeficiency virus RNA. RNA may be detected directly using available procedures, including direct DNA-RNA hybridization. Alternatively, RNA may be copied into DNA by RT-PCR. The human immunodeficiency virus specific RNA transcripts may be unspliced viral MRNA transcripts or spliced viral MRNA transcripts.

In yet another embodiment, the levels of human immunodeficiency virus may be determined by measuring levels of human immunodeficiency virus protein. In a simple assay format, the levels of human immunodeficiency virus protein may be measured by contacting a sample from the patient with a binding protein which specifically binds to a human immunodeficiency virus protein. The amount of binding protein which binds to the human immunodeficiency virus protein is then determined.

In a more preferred embodiment, the binding protein is an antibody. Immunological methods for detecting and measuring the expression of HIV proteins using either specific polyclonal or monoclonal antibodies are known in the art. Examples of such techniques include enzyme-linked immunosorbent assays (ELISAs), radioimmunoassays (RIAs), fluorescence activated cell sorting (FACS), and panning procedures. A two-site, monoclonal-based immunoassay utilizing monoclonal antibodies reactive to two non-interfering epitopes on HIV proteins is preferred, but a competitive binding assay may be employed. These and other assays are well known in the art (82–84).

Preferably, the antibody binds to Nef, Env, or Vpu.

Alternatively, the binding protein may be any non-antibody which binds to HIV. In particular, the binding protein may be a T-cell receptor which binds to HIV, such as CD4.

In a preferred embodiment, the invention is used to determine the presence of HIV in a patient which is being treated with highly active retroviral therapy. In particular, the present method is useful in patients who have no detectable plasma viral load.

Another aspect of the present invention is a kit for determining viral load in a patient infected with human immunodeficiency virus. The kit consists of a first component for separating T cells from a biological sample; a second component for separating $CD4^-CD8^-$ cells from $CD4^+$ or $CD8^+$ cells; and a third component for detecting human immunodeficiency virus.

The first component of the kit is preferably a compound which binds to a T cell specific marker. Examples of T cell specific markers include: $CD2^+$, $CD3^+$, and T cell receptor αβ. The preferred T cell specific marker is $CD3^+$.

In one embodiment of the kit, one or more of the components may be complexed with magnetic beads.

In a preferred embodiment of the kit, the second component has antibodies for $CD4^+$ or $CD8^+$.

The third component of the kit may be a probe for the HIV DNA or RNA or a compound which specifically can identify an HIV protein. Preferred embodiments of the kit include a third component which consists of a probe specific to the genome of HIV. Such probe may be used to detect either the viral RNA or DNA. In an alternative embodiment, the third component of the kit may bind to an HIV protein. A more preferred embodiment of the kit is where the third component consists of an antibody specific to HIV. Alternatively, the third component may consist of a T cell receptor, including CD4.

EXAMPLES

Example 1

Materials and Methods

HIV-HSA viruses.

A plasmid encoding the HIV strain NL4.3 (SI phenotype) with the murine CD24 (mCD24) gene inserted in a XhoI site located in the nef gene was used (15). The plasmid was transfected into the transformed embryonal kidney cell 293 by the calcium phosphate method. After overnight incubation, the supernatant of this culture was used to infect CEM×174 cells. At the time of syncytia formation (after 3 to 5 days), supernatant was harvested and HIV-HSA was titrated for p24 antigen by ELISA (NEN, Renaissance). A single stock of HIV-HSA kept at −70° C. (at p24 10 ng/ml) was used throughout.

Isolation and infection of PBL.

PBL were isolated by density centrifugation with Ficoll-Hypaque (Pharmacia). T-cells were isolated by rosetting with neuraminidase-treated sheep red blood cells. T-cells were infected for 2–3 hours with 5 ng p24 per 1.1 06 T-cells or mock-infected with CEM×174 supernatant in presence of hexadimethrine bromide (10 μg/ml). Infected cells were then cultured for 3–4 days with PHA (1 μg/ml) (Sigma) in RPMI1640 (BioWittaker) supplemented with 10% FBS, L-glutamine (2 mM), 100 μg/ml Streptomycin, 100 I.U/ml Penicillin-G (Gemini Bio-Products) and for another 4–6 days in presence of 10–40 U/ml of rHu-IL-2 (Boehringer-Mannheim) added with fresh media every 2–3 days.

Cell lines.

The following reagents were obtained through the NIH AIDS research and reference reagent program, division of AIDS, NIAID: MAGI-CCR5 from Dr. Julie Overbaugh. MAGI-CCR5 indicator cells constitutively expressing CXCR4 are transfected with CD4 and CCR5 for optimal infection with both T- and and M-tropic HIV strains and with the LTR of HIV linked to the LacZ gene. The LTR is transactivated by viral tat products in the setting of infection (1 6). A β-galactosidase indicator assay can be used for quantification of virus after a single cycle of replication. MAGI-CCR5 cells are fixed with formaldehyde 1%, glutaraldehyde 0.2% for 5' at room temperature, washed and incubated 50' at 37° C. in a staining buffer containing 1 mg/ml X-Gal, 5 mM potassium ferrocyanide, 5mM potassium ferricyanide and 2 mM $MgCl_2$ in PBS.

Immunofluorescence analysis.

The following monoclonal antibodies (mAb) were used: anti-CD4 (clone FFB2.3) or OKT4 (Ortho-Diagnostics). Anti-mCD24 (HSA), anti-CD28, anti-CD30, anti-CD57, anti-CD62L (L-selectin), anti-CD 94, anti-CD95 (Fas) were purchased from Pharmigen. Anti-CD25 (IL-2Ra), anti HLA-A, B, C (HLA class I) and anti-HLA-DR (HLA class II) were purchased from Olympus. Anti-CD11a (LFA-1 α integrin), anti-CD 18 (p2 integrin), anti-CD 44 (Pgp-1), anti-CD45RO, and anti-CD54 (ICAM-1) were purchased from Immunotech or a kind gift from Dr Hioe (New York University). Anti-CD31 (PECAM-1, hec7) was from Dr Muller (C.U.M.C, New York). anti-CD27 (S 152) was from Dr Bigler (Hahnemmann University, Philadelphia), anti-CD29 (β1 integrin, K20), anti-CD49d (α4 integrin, Gil4), anti-CD38 (OKT10) were from Leucocyte Typing V (Fifth International Workshop and Conference, Boston, 3–7 November 1993). The following reagents were obtained through the NIH AIDS research and reference reagent program, division of AIDS, NIAID: anti-CXCR4 (12G5) from Dr James Hoxie (17) and anti-CCR5 (2D7) from Leukosite, Inc. Cells were first incubated for 20' at 4° C. with a biotinylated antibody, washed with PBS 10%FBS, 0.01% sodium azide and incubated with FITC-labeled antibodies. After another wash, cells were incubated with Streptavidin-Tricolor (Caltag) and mCD24 antibody coupled to PE. Cells were then fixed in 1% paraformaldehyde and analyzed using an Epics flow cytometer (Coulter). Immunofluorescent antibodies were carefully titrated and were used separately and in combinations to adjust for proper compensation.

Cell sorting.

Up to $10^7$ HIV-HSA infected cells were stained with 10 μg of purified rat anti-mCD24 antibody (Ml/69, Pharmingen) and sorted as mCD24⁻ and mCD24⁺ populations using magnetic beads, coated with a goat anti-rat IgG (Dynal) at 20 beads per cell for 30' at 4° C. with gentle rolling. The purity of the sorting was greater than 95%. For PCR analysis of CD4 mRNA expression, mCD24+CD4+ and mCD24+CD4− cells were sorted using a FACSVantage (Becton Diskinson), and the purity of the sort was greater than 98%.

Genomic DNA and cDNA preparation.

Genomic DNA was prepared by lysing cell pellets in 0. 1 M Tris-Ci, 10 mM EDTA, and 600 μg/ml proteinase K at 56° C. for an hour followed by 95° C. for 15'. Total RNA was prepared using RNAzol (Biotecx) and cDNA synthesis was done using hexamer random primers and MULV reverse transcriptase according to the manufacturer instructions (Pharmacia).

PCR amplification.

10 μl of gDNA or cDNA was used in a 50 μl PCR reaction containing 12.5 pmol of each primers, 10 mM Tris-HCl, 50 mM KCl, 0.01%gelatin, 0.1% Triton X-100, 0.1 mM dNTPs, IU Taq polymerase and either 1.5 mM or 3mM MgCl12 for cDNA or gDNA PCRs, respectively (Promega). Sensitivity of the technique was increased by addition of 2.5 μCi of [α-$^{32}$P] dCTP (Arnersham) per PCR. Primers sequences were as followed: HIV-1 gag SK 38 (sense) and HIV-1 gag SK 39 (anti-sense) have been previously described (18); actin mRNA (sense), 5'-CCTCATGAAGATCCTCACCG-3'(SEQ. ID No. 1); actin mRNA (anti-sense), 5'-AAGGAAGGCTGGAAGAGTGC-3'(SEQ. ID No. 2); CD4 mRNA (sense) 5'-TGGACATGCACTGTCTTGC-3' (SEQ. ID No. 3); CD4 mRNA (anti-sense) 5'-GGTGATCCAAGACTTGGAGG-3' (SEQ. ID No. 4). The primers and PCR conditions for multi-spliced and un-spliced HIV mRNA were used as described elsewhere (19). PCR conditions were as follows: HIV-1 gag-DNA, one cycle at 94° C. for 2 min., and 28 to 32 cycles at 94° C. for 30s, 60° C. for 30s, 72° C. for 60s; actin and CD4 mRNA, one cycle at 94° C. for 3 min., and 28 to 32 cycles at 94° C. for 60s, 60° C. for 60s, 720 C for 60s. 10 μl of each PCR reaction was run in a 8% acrylamide gel and detected by autoradiography.

Example 2

Reporter Gene Expression and HIV Infection in Peripheral Blood Lymphocytes

To determine whether HIV-HSA could be used for accurate single cell detection of only those T cells that are productively infected, PBL from a normal donor were infected with increasing amounts of HIV-HSA (FIG. 3A). mCD24⁺ cells were present on day 8 p.i. at a frequency increasing from 0.1 to 8.9% with increasing inoculum. No mCD24⁺ cells were seen in the absence of viral infection, showing that the antibody against mCD24 did not cross react with human antigens expressed on PBL. Infection of primary lymphocytes with 5 ng of HIV-HSA gave a frequency of infected cells of less than 10%, in good agreement with frequencies of infected cells determined ex vivo (20), and this dose was used in subsequent experiments.

Figure 4A:
FIG. 4 shows views of the cultured cells. After eight days in culture, $mCD24^+$ cells were positively sorted with magnetic beads and plated directly onto 40–50% confluent cultures of MAGI-CCR5 in DMEM 10% FBS supplemented with IL-2 (20 U/ml) for two days. Based on the percentages of $mCD24^+$ cells and a sorting efficiency of 95%, $10^5$ cells were plated. $10^5$ $mCD24^-$ cells were plated in parallel. Shown are cultures with $mCD24^+$ cells from donor 1 (FIG. 4A) and 2 (FIG. 4B) (40×magnification) and donor 1 at higher magnification (FIG. 4C) (100×). Cultures with $mCD24^-$ cells from donor 1 (FIG. 4D) and 2 (FIG. 4E) and a control culture of MAGI-CCR5 in media alone show background $\beta$-gal activity (FIG. 4F) (40×). Note that $mCD24^+$ cells complexed with magnetic beads gave foci of infected MAGI-CCR5 (FIG. 4C).
Figure 4D:
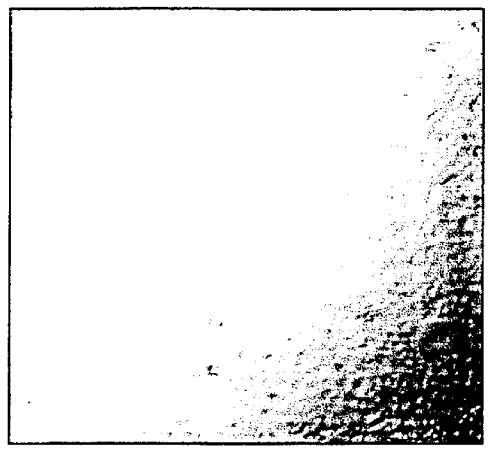
Figure 4B:
Figure 4E:
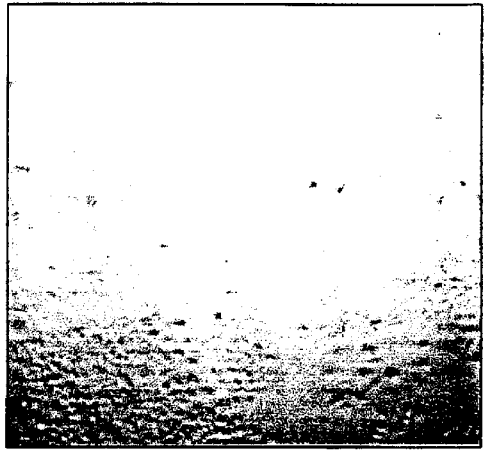
Figure 4C:
Figure 4F:
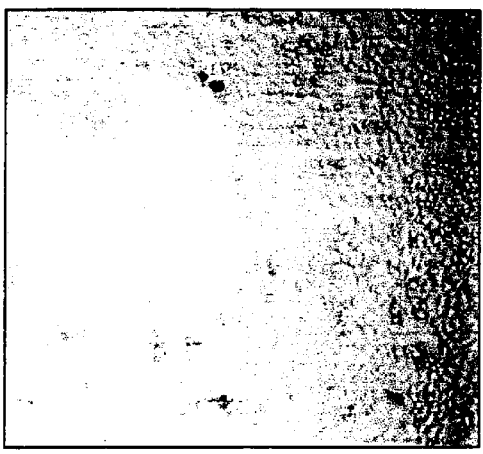

HIV-gag DNA proviral copies and RNA transcripts were then measured in mCD24⁺ and mCD24⁻ subsets (FIG. 3B). HIV-gag DNA was present in both subsets. In contrast, at similar intensities of actin PCR bands, HIV multi-spliced and un-spliced RNA were exclusively detected in the mCD24⁺ sample (FIG. 3B, compare lanes 3 and 5 or lanes 4 and 6). This shows that cells productively infected with the reporter virus efficiently expressed mCD24. Productive infection of mCD24⁺ and mCD24⁻ T cells was further tested using MAGI-CCR5 indicator cells (FIG. 4). MAGI-CCR5 cells infected with HIV (blue cells) were easily detectable when co-cultured with mCD24⁺ cells (FIGS. 4A, B and C). In contrast, co-cultures with mCD24⁻ cells (FIGS. 4D and E). or without added lymphocytes (FIG. 4F), were similar with very low numbers of blue cells.

Figures 5A, 5B:
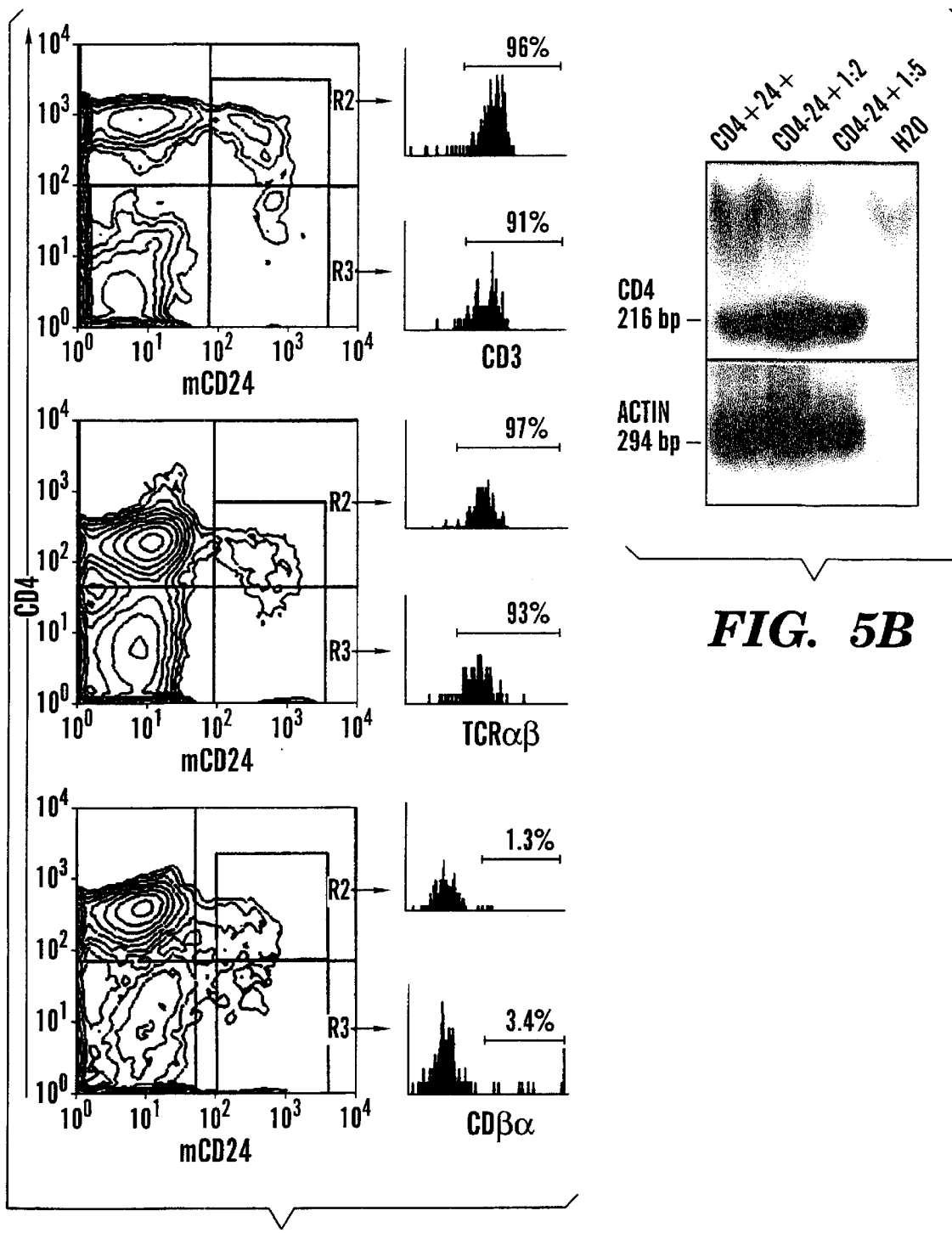
FIG. 5A shows representative staining of primary lymphocytes infected in vitro with HIV-HSA and analyzed for CD3 (upper panels), TCR-αβ (middle panels), and CD8 (lower panels), within mCD24+CD4+(R2) and mCD24+CD4−(R3) cells at day 10 p.i.
FIG. 5B shows the results of RT-PCR amplification of CD4 and actin cDNA from the indicated subsets. Primary T cells infected with HIV-HSA in vitro were sorted at day 10 p.i. and analyzed for CD4 and actin mRNA as described in the methods. Indicated cDNA dilutions were chosen to obtain similar intensities of actin PCR bands.

Productively HIV-infected T cells (mCD24⁺) showed a progressive decrease in CD4 expression, suggesting that HIV-induced downregulation of CD4 from the cell surface occured in the culture (FIG. 3A). This apparent downregulation was discernible in cells infected with virus corresponding to 1 ng p24 gag but was more pronounced in those infected with 5 ng p24 gag (CD4⁻ cells among mCD24⁺ cells represented 15% and 33%, respectively), suggesting that mCD24⁺CD4⁻ cells derived from mCD24⁺CD4⁺ cells. This is further indicated by detection of CD4 mRNA by PCR in mCD24+CD4− cells isolated by cell sorting (FIG. 5B). Furthermore, mCD24+CD4− and mCD24+CD4+ cells were negative for the expression of the CD8 coreceptor, and expressed similar amounts of CD3 and TCR-αβ molecules, (FIG. 5A) The extent of CD4 down regulation was similar with OKT4 anti-CD4 mAb, which does not compete with gp120 for binding to CD4 (21), ruling out CD4 epitope masking by gp120 in this system. Together, these results demonstrate that during the first few rounds of HIV-HSA replication in primary lymphocytes, mCD24 expression was an efficient marker for productively HIV-infected cells.

Example 3

Apoptosis of Productively HIV-infected T Cells

Figure 6A:
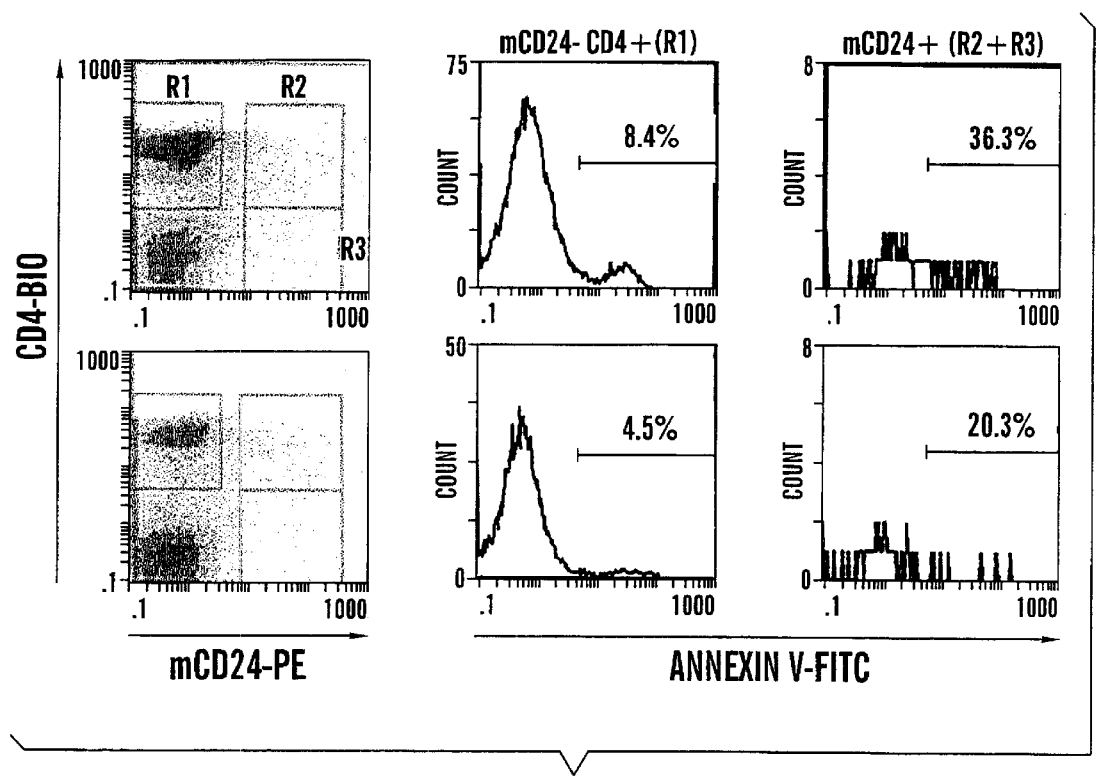
FIG. 6A shows T cell subsets which were defined as mCD24−CD4+ cells (R1), mCD24+CD4+ cells (R2) and mCD24+CD4− cells (R3). Representative staining with annexinV-FITC, CD4-Bio and mCD24-PE of primary lymphocytes from two different donors, infected with HIV-HSA after 10 days in culture.
Figure 6B:
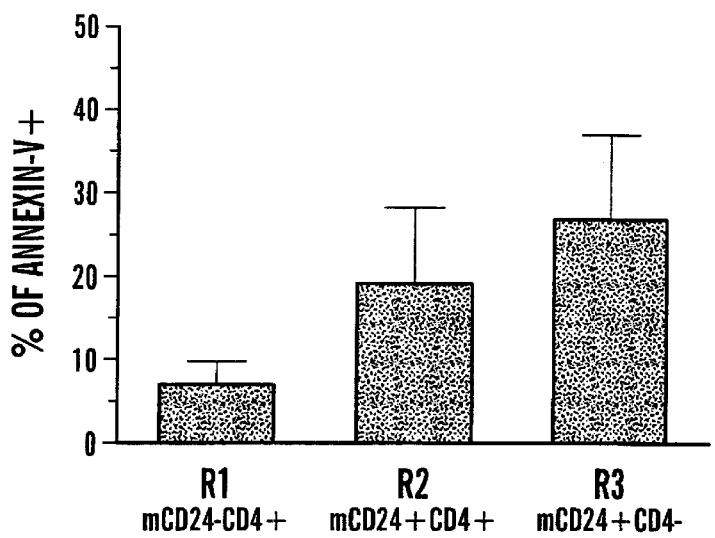
FIG. 6B shows Annexin-V binding on mCD24−CD4+ T cells (R1), mCD24+CD4+ cells (R2) and mCD24+CD4− T cells (R3). Shown are the mean values of the frequencies of annexinV+) cells among the indicated subsets ±standard deviation (n=9), measured on day 7–13 p.i.

Apoptosis may influence cell surface expression of various molecules and that could possibly interfere with phenotypic analyses. Thus, primary lymphocytes, infected with HIV-HSA, were analysed for annexin-V binding, as an indicator of early apoptotic cell death. For this analysis, three populations of cells were defined: mCD24⁻CD4⁺ (R1), mCD24⁺CD4⁺ (R2), mCD24⁺CD4⁻ (R3) (FIG. 6A). A significant enrichment in annexinV⁺ cells was seen in the mCD24⁺ subsets compared with mCD24⁻CD4⁺ T cells (FIG. 6A). Less than 40% of productively HIV-infected T cells bound annexin-V (FIG. 6B). Therefore, the phenotypic characterisation of productively infected cells described below applies to viable cells.

Example 4

Altered Expression of Cell Surface Molecules with Productive Infection

Whether mCD24 expression was associated with modulation of cell surface antigens other than CD4 was then tested. Expression of molecules related to antigen presentation (HLA class I and class II), cell activation (CD25, CD28, CD30, CD38, CD44, CD45R0, CD57), trafficking and homing (CD11a, CD18, CD31, CD49d, CD29, CD54, CD62L, CXCR4, CCR5), members of the TNF-receptor superfamily (CD27, CD95) and an NK-related signalling molecule (CD94) was monitored within the three populations mCD24⁻CD4⁺ (R1), mCD24⁺CD4⁺ (R2), and mCD24⁺ CD4⁺ (R3), as defined in FIG. 7.

Figure 7:
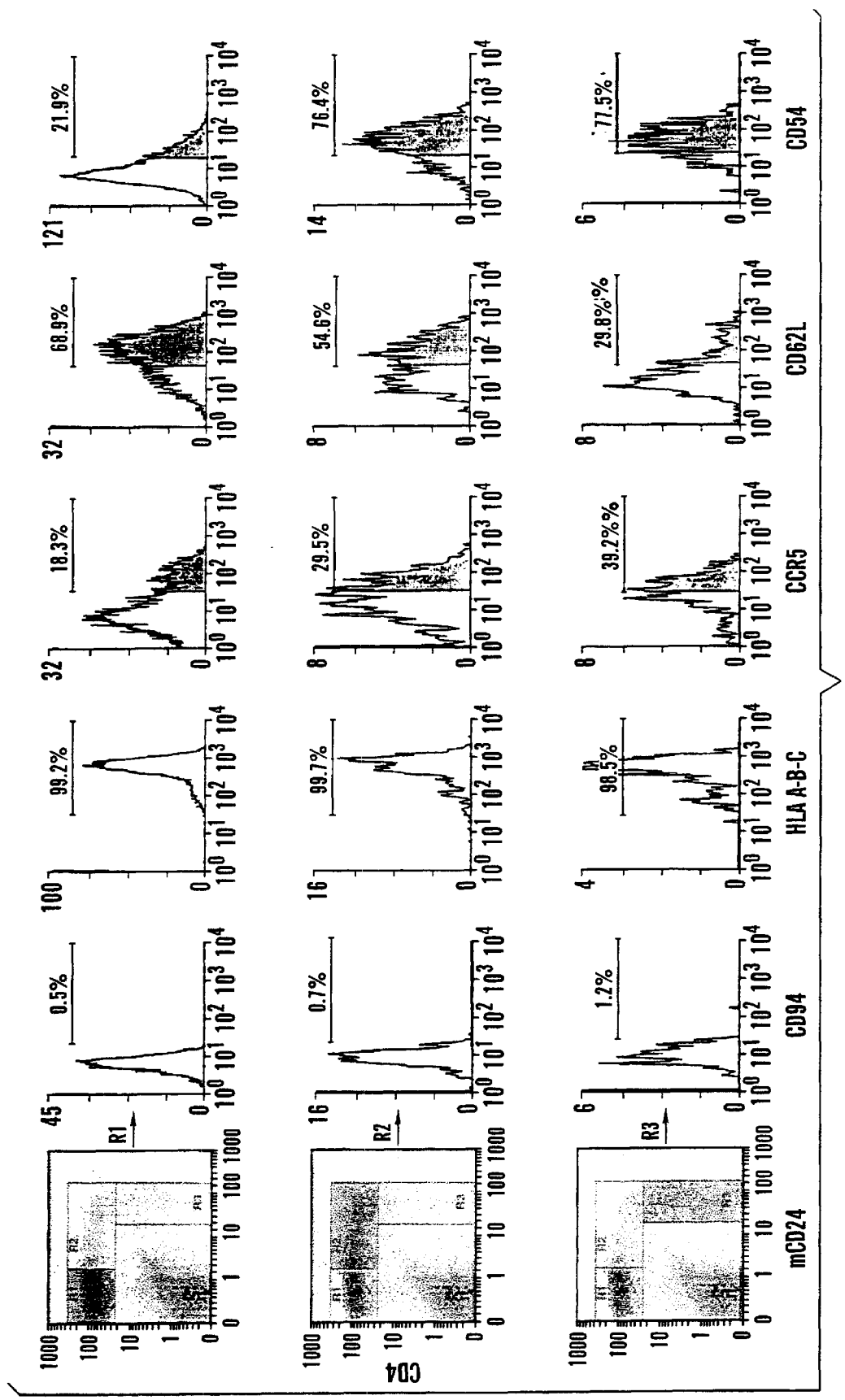
FIG. 7 shows representative staining among primary lymphocytes infected with HIV-HSA. (Left panels) T cell subsets were defined as mCD24−CD4+ cells (R1), mCD24+CD4+ cells (R2) and mCD24+CD4− cells (R3) (see shaded area). Representative staining and frequencies of cells expressing CD94, HLA class I, CCR5, CD62L and CD54 molecules at D7 p.i are shown as histograms.
Figure 8B:
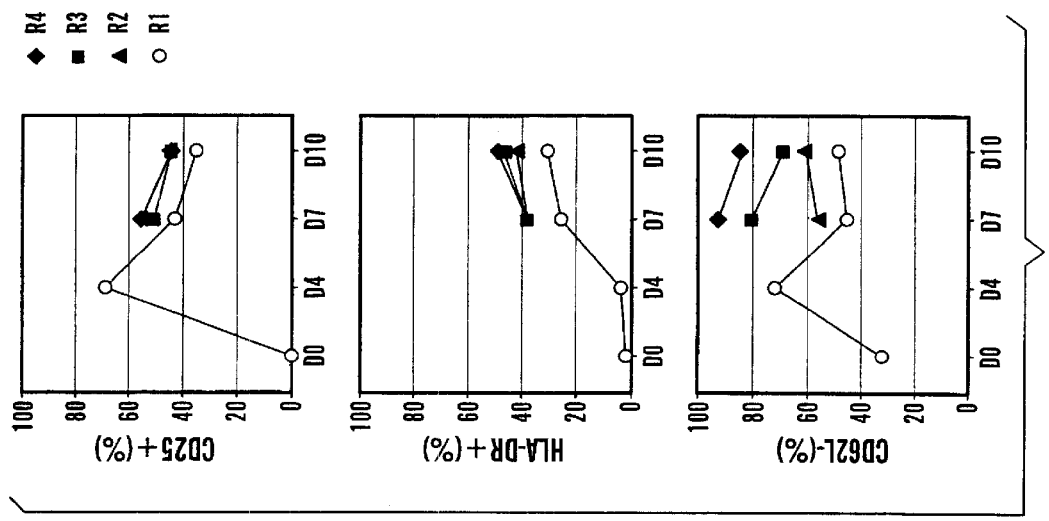
FIG. 8B shows the comparative expression of CD25, HLA-DR and CD62L in subsets gated in FIG. 6A. At the indicated time points cells were stained with anti-CD4 (biotinylated) and anti-mCD24 (PE) and either anti-CD25, anti-HLA-DR or anti-CD62L antibodies (FITC-labeled). Curves shown are the mean of the percentages from cells of two donors analysed in parallel within R1 (open circles), R2 (filled triangles), R3 (filled squares) and R4 (filled diamonds). Weak or absent expression of mCD24 before day 7 precludes accurate measurements. Similar results were obtained in two other experiments.

Expression of CD94 and HLA class I was respectively negative and positive in all populations of T cells defined by CD4 and mCD24 (FIG. 7, Table 1).

a grossly different activation status among the various mCD24⁺ populations, since the frequencies of expression of activation antigens CD25 and HLA-DR were not significantly altered in these populations (Table I). Seventy percent of CD4⁺ cells became CD25⁺ by day 4 (FIG. 8B). By day 7, the proportion of these cells dropped to 40%. On days 7

TABLE 1

|  | HLA-A, -B, -C | CXCR4 | CD62L | CD25 | CCR5 | HLA-DR | CD94 |
|---|---|---|---|---|---|---|---|
| mCD24⁺CD4⁺ | 99.65 ± 0.5 | 74.8 ± 24.4 | 86.0 ± 6.8$^b$<br>66.3 ± 12.3$^c$ | 59.5 ± 2.65 | 15.8 ± 7.6 | 20.8 ± 11.0 | 0.4 ± 0.4 |
| mCD24⁺CD4⁺ | 99.5 ± 0.8 | 78.2 ± 14.5 | 73.4 ± 4.4$^{b,d}$<br>36.0 ± 9.6$^{c,d}$ | 61.25 ± 24.7 | 45.9 ± 10.3$^d$ | 36.3 ± 15.0 | 1.6 ± 1.2 |
| mCD24⁺CD4⁺ | 99.6 ± 0.5 | 73.6 ± 5.7 | 46.7 ± 6.1$^{b,d}$<br>19.9 ± 2.5$^{c,d}$ | 57.5 ± 20.0 | 46.0 ± 7.7$^d$ | 31.3 ± 22.0 | 0.9 ± 0.9 |

$^a$Results represent frequencies of cells expressing the indicated molecule (column headings) within populations of primary lymphocytes (left column entries) defined in FIG. 5. Results were obtained on day 7 postinfection, using six different donors, except for CD62L, for whom day 7 and day 10 results are shown. Results for CXCR4 and CCR5 expression were obtained between days 8 and 12 from two donors in three different experiments.
$^b$Day 7 results.
$^c$Day 10 results.
$^d$p < 0.05 as determined with an independent 1 test for comparisons with the mCD24⁺CD4⁺ population.

Only a minority of CD4⁺ T cells (mean 15%) expressedCCR5, as previously reported (22). However, expression of CCR5 was more frequent among productively infected cells than among mCD24⁻ cells at day 7 and day 10 after infection (FIG. 7, Table 1). This increase in frequency of CCR5-expressing cells was mirrored by a 2.5-fold increase in the mean fluorescence units (MFU) of CCR5 in mCD24+cells. It is unlikely that enrichement in CCR5⁺ cells in productively HIV-infected T cells is due to the role of CCR5 as a HIV-1 co-receptor, because HIV-HSA is a T-cell tropic virus which uses exclusively CXCR4 as its co-receptor (23). Expression of CXCR4 was ubiquitous on activated CD4⁺ T cells, as previously reported (24). No differences in the expression of CXCR4 could then be observed between mCD24⁻ and mCD24⁺ populations (Table I).

Primary T cells productively infected with HIV were enriched for CD54⁺ cells (FIG. 7), in contrast with a previous report describing a loss of CD54 expression on a human lymphoblastoid T-cell line infected with HIV 25). This upregulation of CD54 on productively HIV infected T cells was detected as early as day 7 after infection and was still detectable at day 9 after infection.

Figure 8A:
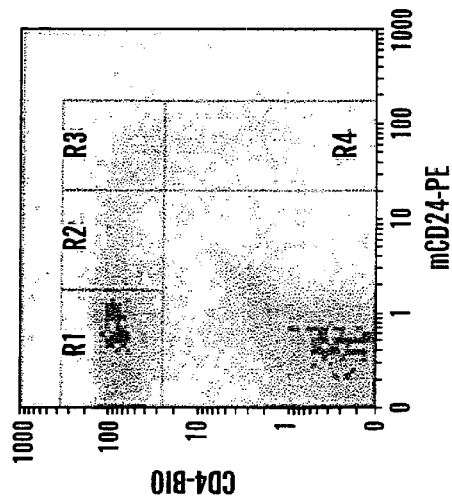
FIG. 8A shows the definition of T cell populations based on mCD24 and CD4 expression. PBL were infected and stimulated as described in materials and methods and analyzed at day 8 after infection. Gates were set around mCD24−CD4+ (R1), mCD24$^{lo}$CD4+ (R2), mCD24$^{hi}$CD4+ (R3) and mCD24$^{hi}$CD4− (R4).
Figure 8C:
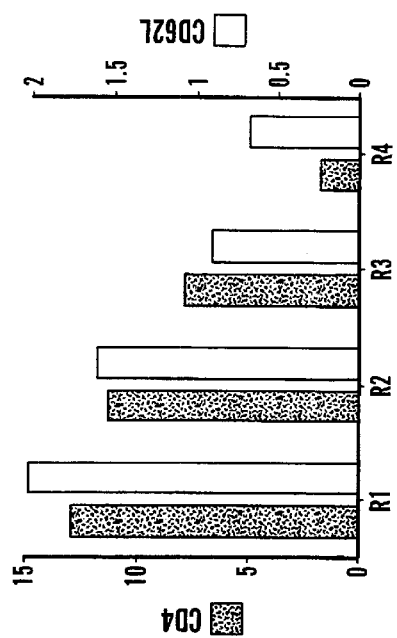
FIG. 8C shows the fluorescence in Mean Flourescence Units (MFU)of CD4 and CD62L. Results represents the mean of the MFU obtained at day 7 p.i from two individuals for CD62L and CD4 expression in subsets gated in FIG. 6A. Note the gradual loss of CD62L expression with the loss of CD4 expression.

In cells productively infected with HIV, expression of CD62L (L-selectin) was selectively decreased as early as day 7 p.i. (FIG. 7, Table 1). This loss was more complete at day 10 p.i. (Table I). This decrease in the frequency of CD62L-expressing expressing cells was mirrored by a 2-fold decrease in the MFU of CD62L in mCD24+CD4+ cells, and by a 4-fold decrease in mCD24+CD4− cells, when compared with mCD24−CD4+ cells. After an initial increase in CD62L⁻ cells due to PHA stimulation, the proportion of CD4⁺CD62L⁻ T cells returned to baseline levels in mCD24⁻ cells (FIG. 8B). In the mCD24⁺ population, the proportion of CD62L⁻ cells remained elevated. This result suggested that loss of CD62L expression at the cell surface of productively infected T cells may result from a defect in the re-expression of this molecule. As illustrated in FIG. 8C, the loss of CD62L correlated with the loss of CD4 expression. Persistent loss of CD62L expression was most pronounced in gated regions R4>R3>R2>R1. Thus, productively infected cells gradually lose expression of CD4 and CD62L in concert. The loss of CD62L could not be accounted for by and 10, CD25⁺ cells were enriched by ~10% in the mCD24⁺ subsets compared with the mCD24⁻CD4⁺ subset. However, no differences in the proportion of CD25⁺ cells were detected among the three populations of mCD24⁺ cells defined in FIG. 8A. The proportion of CD4⁺HLA-DR⁺ cells increased shortly after addition of IL-2 to the culture. HLA-DR⁺ cells were also enriched by ~10% within the mCD24⁺ populations. Again, there was no difference in the proportion of HLA-DR⁺ cells between mCD24⁺ populations. Therefore persistent lack of CD62L expression is a feature of T cells in which HIV is actively replicating and is independent of the activation status of mCD24⁺ subsets.

After 8 days in culture, CD11a, CD18, CD27, CD28 CD29, CD44, CD45RO, CD49d and CD95 were expressed on most cells (>90%), regardless of mCD24 expression. Expression of CD30, CD31 and CD57 was rare in these cultures (<20%) and did not correlate with mCD24 phenotype.

Together the results suggest that CD4, CD62L, CD54 and CCR5 expression are specifically modified at the cell surface of productively HIV-infected T cells.

HIV and host cellular proteins are involved in complex interactions during infection. There are many examples of viral gene products directly affecting expression or function of host cell proteins. For example, nef may exert its effect on CD4 and HLA class I expression through association with the AP-2 adaptor protein complex, which may facilitates endocytosis of these host cell molecules (26). It is therefore likely that HIV infection may interfere with the expression of additional molecules, other than CD4 and HLA class I. In the present study, cell surface changes directly associated with productive infection were analysed. Productively HIV-infected primary T cells detected with a reporter virus were analysed for cell surface expression of several molecules of immunological interest. The results showed that productive HIV-infection was associated with increased CD54 and CCR5 expression while CD62L and CD4 expression was progressively and simultaneously lost. HIV-HSA lacks nef and yet induces CD4 down regulation on primary lymphocytes. This confirms that nef is not an absolute requisite for CD4 down regulation (27). Furthermore, these results suggests that nef is not required for the observed changes on the surface of T cells productively infected by HIV. To the contrary, down regulation of MHC class I molecules was not observed with HIV-HSA, confirming that Nef is absolutely required in this case (4).

Activated T cells are a prime target for HIV infection and T cell activation is required for productive infection (28–30). Among HIV expressing cells, no significant increased expression of the activation antigens CD25 and HLA-DR was found. In contrast, HIV expressing cells were enriched in cells with persistent lack of CD62L expression and with increased CCR5 expression, thereby resembling cells of a "memory" phenotype. However, several lines of evidence argue against preferential infection of "memory" T cells by HIV-HSA in the experiments. HIV-HSA is derived from the T-tropic NL4.3 strain which exclusively use CXCR4 as a coreceptor (23). Therefore, HIV-HSA could not preferentially infect T cells based on CCR5 expression. Moreover, loss of CD62L occured simultaneously with loss of surface CD4. As the mCD24+CD4− appear to derive from mCD24+ CD4+ precursors, it is unlikely that the virus selectively infects "memory" CD62L− cells from the onset. The predominance of HIV replication in "memory" T cells (31–33) could then be explained by HIV inducing phenotypic changes typical of "memory" T cells.

If it is not preferential infection, what then could be the cause for the CCR5$^+$CD54$^+$ and CD62L$^-$ phenotype observed in some HIV expressing cells? Virus-specific phenotypic modifications detected in the study may originate from a direct effect of viral proteins on CCR5, CD54 and CD62L metabolism, as described for CD4 (11), or may come from interference of viral proteins with host proteins that regulate the expression of CCR5, CD54 and CD62L. Cell surface phenotypic modifications can also be explained by indirect effect of cytokines on HIV expression. HIV-HSA may have used CXCR4 as a co-receptor to infect cells, but then HIV expression was stimulated in cells that also expressed the β-chemokine receptor CCR5. This hypothesis implies that signalling through CCR5 has a positive effect on HIV expression. To date, such a positive effect of the β-chemokines MIP-1α, MIP-1β and RANTES on HIV replication has not been reported. In fact, MIP-1α, MIP-1β and RANTES are better known to inhibit HIV replication in vitro (34–35) and high levels of β-chemokine secretion have been found in individuals resistant to HIV-1 infection, independently of the CCR5 genotype (36). Nevertheless, β-chemokines have the ability to co-stimulate T cells through induction of CD25 expression and IL-2 production (37) and that could increase HIV expression. The results showed that CD25$^+$ cells were not significantly enriched among productively HIV-infected cells. Thus, stimulation of HIV expression due to IL-2 or β-chemokines is an unlikely explanation for increased CCR5 expression among productively HIV-infected T cells. It seems likely that unidentified HIV proteins may modify CCR5 biosynthesis or degradation, resulting in increased expression. To date, HIV has not been reported to affect CCR5 expression.

The loss of CD62L expression may occur at the transcriptional or post-transcriptional level (38) or at the level of shedding from the cell surface due to specific metalloprotease (39). Expression of CD62L MRNA was still detectable in mCD24$^+$ cells. Therefore, the loss of CD62L on mCD24$^+$ cells may be due to post-transcriptional regulation. HIV infection has been reported to stimulate synthesis and secretion of a metalloprotease, the 92 kDa type IV collagenase (40). Because the re-expression of CD62L was impaired at the cell surface of productively HIV-infected T cells, it is possible that HIV replication prevents re-expression of CD62L after activation, perhaps by directly or indirectly modulating metalloprotease activity.

CD62L is key to binding of lymphocytes to high-endothelial venules allowing transmigration through the endothelium and migration in to the peripheral lymph node (41). In addition, L-selectin deficient mice have impaired recruitment of lymphocytes into inflammatory sites (42), contributing perhaps to a delay in primary T cell responses (43). Loss of CD62L on some productively HIV-infected T cells may subvert their homing to lymph nodes.

The β-chemokines are potent chemoattractants for T cells (44). For example, preferential migration of human T cells to the skin in response to RANTES (45) and in the thymus in response to MIP-1β (46) was observed in SCID mice reconstituted with human lymphocytes. Therefore, upregulation of CCR5 is likely to change the homing pattern of productively infected cells.

CD54 is normally expressed at low levels on resting T cells but is upregulated on activated T cells. Increased expression of CD54 on productively HIV-infected T cells may enhance their interaction with CD11a, CD11b or CD11c-expressing cells, the natural ligands for CD54 (47), Indeed, antibodies against LFA-1 inhibit syncitia formation betweeen an infected cell line and PHA-blasts, suggesting a role of LFA-1/CD54 interaction in cell to cell transmission of HIV (48). The interaction between CD54, expressed on endothelium, and LFA-1, expressed on T cells, is crucial for efficient trans-migration of T cells through vascular endothelium (47). The role of CD54 expression on activated T cells is less well understood but high expression of CD54 on productively HIV infected T cells could influence their transendothelial migration.

It is striking that, of the 21 cell surface molecules analysed in the previous examples, only three were modified by productive infection, other than CD4, and that they relate to T cell trafficking and homing. The results suggests that some productively infected cells expressing CD54, CCR5 but lacking CD62L may have specific homing characteristics. It is tempting to speculate on the possible implications of these results in vivo. Since β-chemokines are inflammatory molecules (49), productively HIV-infected cells might be preferentially attracted on sites of inflammation and their high expression of CD54 may facilitate transmigration through the endothelium and/or cell to cell transmission. Because of down regulation of CD62L, homing of productively HIV-infected T cells may be at other sites than lymph nodes. As an example, it has recently been reported that SIV-infected cells are preferentially found in the gut of infected animals during the acute phase of infection (50). Whether certain tissues like the gut might provide a sanctuary for HIV is a question for the future.

Example 5

Materials and Methods for Examples 6–9

Human Subjects.

Informed consent was obtained from patients at various New York Hospital clinics. The clinical parameters given in Table 2 are those at the time of study, unless indicated otherwise. Patients were placed in two groups as defined by response to HAART (see Table 2). Significance was determined by t test. A separate nonoverlapping cohort of patients was examined (see FIG. 12 and Table 3).

TABLE 2

Clinical characteristics of patients

| HIV DNA in cell type | Patients* | Age, years | Gender† | CD4 count per mm‡ | Viral load, copies per ml§ | Present medications§ | | | | Duration of present treatment, months (or year of diagnosis) | Response to HAART¶ |
|---|---|---|---|---|---|---|---|---|---|---|---|
| | | | | | | PI | NRT | NNRT | Other | | |
| CD4 | CSS9 | 44 | M | 257 | <400 | 1 | 1 | 1 | — | 4 | + |
| | CSS12 | 37 | M | 522 | <400 | 1 | 2 | — | — | 7 | + |
| | H1 | 41 | M | 659 | 4,266 | — | — | — | — | Naive (1985) | NA |
| | Met91 | 43 | F | 268 | 36,349 | — | — | — | — | Naive (1990) | NA |
| CD4 DN | CSS22 | 33 | M | 241 | 632 | 1 | 2 | 1 | — | 6 | + |
| | CSS25 | 37 | F | 265 | 1,318 | 1 | 2 | 1 | — | 3 | + |
| | CSS21 | 36 | M | 437 | <400 | 1 | 2 | — | — | 22 | + |
| | CSS8.1 | 44 | M | 717 | 546 | — | 3 | — | — | 8 | + |
| | CSS8.2 | — | — | 595 | <400 | — | 3 | 1 | — | 6 | + |
| | CSS10 | 34 | F | 337 | <400 | 1 | 2 | — | — | 11 | + |
| | CSS15 | 53 | M | 469 | 18,109 | 1 | 2 | — | — | 1 | + |
| | CSS13 | 39 | M | 92 | <500 | 1 | 2 | — | — | 7 | + |
| | CSS23 | 44 | M | 287 | <25 | 1 | 2 | — | T | 18 | + |
| | CSS26 | 25 | T | 96 | 198,996 | — | — | — | — | Naive (1995) | NA |
| | Met70 | 44 | M | 354 | 15,930 | 1 | 2 | — | — | 6 | − |
| | Met90.1 | 39 | M | 253 | 64,000 | 1 | 1 | — | T | 1 | − |
| | Met90.2 | — | — | 195 | 53,000 | 1 | 1 | — | T | 2 | − |
| | Met90.3 | — | — | 220 | <400 | 1 | 2 | 1 | T | 7 | + |
| CD4 DN CD8 | CSS19 | 47 | M | 518 | 157,000 | — | — | — | Z1 | 1 | − |
| | CSS20 | 38 | M | 141 | 121,292 | — | — | — | — | — | − |
| | CSS24 | 39 | T | 303 | >1,000,000 | — | 1 | 1 | — | 2 | − |
| | CSS3 | 47 | M | 146 | 100,479 | — | — | — | — | — | − |
| | CSS18 | 36 | F | 965/363 | <400/233,272 | 1 | 3 | — | — | 5 | NA |
| | CSS16.1 | 45 | M | 388 | 9,000 | — | — | — | — | Naive (1991) | NA |
| | CSS16.2 | — | — | 566 | 11,498 | — | — | — | — | — | NA |

Footnotes for Table 2
Patients are arranged in three groups: HIV detectable (i) only in CD4 and DN, (ii) in CD4 and DN, and (iii) in CD4, DN and CD8. For CSS23 (see below), one experiment (shown in FIG. 2A) revealed HIV DNA only in DN cells, but in another experiment, HIV DNA was also found in CD4 T cells.
*CSS denotes patients from an AIDS clinic at New York Hospital (NYH); Met denotes a methadone maintenance clinic at NYH; and H denotes a hemophilia clinic at NYH.
†M, male; F, female; T, transgender (genetic male on female hormones).
‡Viral copies per ml were assessed by RNA PCR (Roche Diagnostics), or by bDNA assay (Chiron) in CSS23. When two values are indicated (CSS18), the experimental sample was obtained within a few months in between.
§The number of HAART medicines within each class of drugs is indicated. PI, protease inhibitors (Crixivan, indinavir; Viracept, nelfinavir; Inviras, saquinavir); NRT nucleoside RT inhibitors (Zidovine, AZT; Zerit, D4T; Epivir, 3TC; Hivid, DDC; Videx, DDI); NNRT, nonnucleotide RT inhibitors (Viramune, nevirapine; Rescriptor).
¶Response to HAART is defined as >70% decrease in the viral load or consistently undetectable viral load. NA, not applicable.

TABLE 3

Viral RNA in T cell subsets.

| Patient | HIV per ml | CD4 per mm³ | Subset | Actin | US | MS | No. cells × 10⁶ | Percentage of DN cells per total CD3⁺ cells | Overnight culture | IL-2 |
|---|---|---|---|---|---|---|---|---|---|---|
| m140 | 3,000 | 413 | DN | + | − | − | 1.19 | 5.5 | | |
| | | | CD4 + CD8 | + | − | − | 20.30 | | | |
| m38 | 60,251 | 93 | DN | + | − | − | NA | | | |
| | | | CD4 + CD8 | + | − | − | NA | | | |
| c145 | 462 | 233 | DN | + | − | − | 0.19 | 11.2 | Y | Y |
| | | | CD4 + CD8 | + | − | − | 1.50 | | Y | Y |
| c150 | <400 | 528 | DN | + | − | − | 2.59 | 11.3 | Y | Y |
| | | | CD4 + CD8 | + | − | − | 20.3 | | Y | Y |
| c151 | 3,117 | 375 | DN | + | − | − | 0.13 | 9.8 | Y | Y |
| | | | CD4 + CD8 | + | − | − | 1.19 | | Y | Y |
| m17 | <400 | 340 | DN | + | + | − | 0.09 | 6.3 | Y | Y |
| | | | CD4 + CD8 | + | + | + | 1.33 | | Y | Y |
| c146 | <400 | 887 | DN | + | + | + | 0.19 | 4.9 | Y | Y |
| | | | CD4 + CD8 | + | − | + | 3.70 | | Y | Y |
| c147 | <400 | 373 | DN | + | − | + | 1.81 | 8.0 | Y | |
| | | | CD4 + CD8 | + | + | + | 20.90 | | Y | |
| m122 | <400 | 557 | DN | + | + | − | 0.57 | 1.9 | Y | Y |
| | | | CD4 + CD8 | + | + | − | 30.1 | | Y | Y |
| | | | DN | + | − | + | 0.57 | | | |
| | | | CD4 + CD8 | + | (+) | + | 30.1 | | | |

TABLE 3-continued

Viral RNA in T cell subsets.

| Patient | HIV per ml | CD4 per mm³ | Subset | Actin | US | MS | No. cells × 10⁶ | Percentage of DN cells per total CD3⁺ cells | Overnight culture | IL-2 |
|---|---|---|---|---|---|---|---|---|---|---|
| c149 | 8,047 | 185 | DN | + | + | + | 0.94 | 5.9 | Y | Y |
| | | | CD4 + CD8 | + | + | + | 15.0 | | Y | Y |
| | | | DN | + | (+) | + | 0.94 | | | |
| | | | CD4 + CD8 | + | + | + | 15.0 | | | |

The presence of detectable actin mRNA, HIV multispliced mRNA (MS), and HIV unspliced mRNA (US) in the subsets (see Methods; DN, CD4⁺CD8⁺CD3⁺; CD4 + CD8) is indicated by +. (+) indicates that some experiments gave negative results. The cell numbers used to prepare the RNA from the isolated subset are indicated. The relative percentage of DN cells per total CD3⁺ cells, clinical data on plasma viral load, and CD4 counts are also indicated. Some samples (indicated by Y) were cultured overnight in medium containing FCS with or without recombinant human IL-2. Each sample was analyzed at least twice.

Cell-Sorting Strategy and Efficiency.

Figure 9:
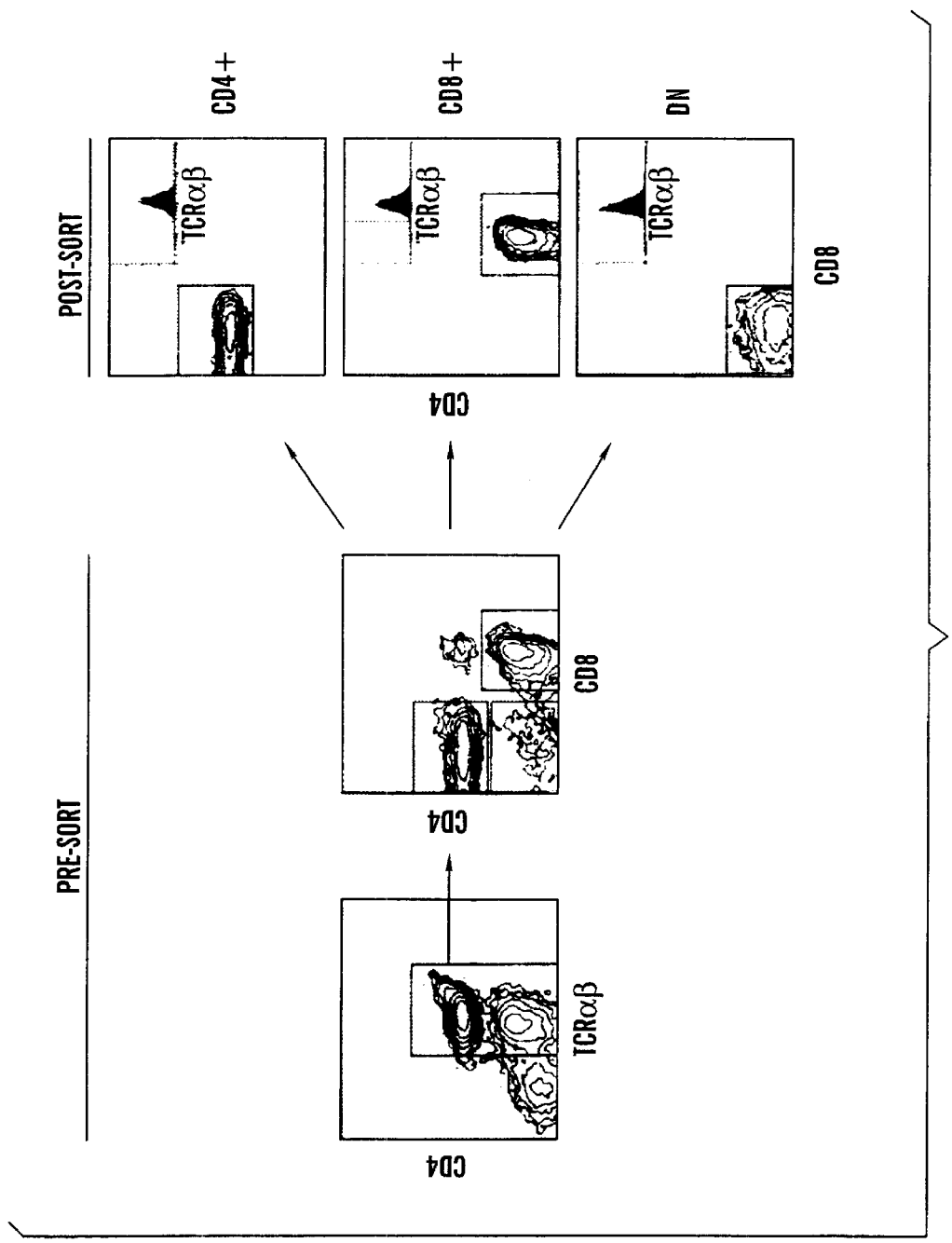
FIG. 9 depicts the cell-sorting strategy and efficiency. Presort gates were set around TCR+ cells. Subsequently, CD4+CD8+, CD4−CD8− cells were sorted. Typically, the purity for the sorted T cells subsets exceeded 98%, and the sorted subsets were virtually all TCR-αβ+.

PBL were isolated on Ficoll/Hypaque (Amersham Pharmacia) and stained with optimal dilutions of anti-CD4-biotin (clone FFB2,3), anti-TCR-$\alpha\beta$-FITC (T10B9, PharMingen), and anti-CD8-phycoerythrin (HIT8$\alpha$, PharMingen). Cells were incubated for 20 min at 4° C. with CD4-biotinylated antibody, washed with PBS/10% (vol/vol) FBS/0.01% sodium azide, incubated with anti-TCR-FITC antibody, washed again, incubated with Streptavidin-Tricolor (Caltag, South San Francisco, Calif.) and CD8-phycoerythrin antibody, and finally fixed in 1% paraformaldehyde. Gates were set as indicated in FIG. 9 for sorting with a fluorescence-activated cell sorter. (FACSvantage, Becton Dickinson).

HIV gag DNA PCR.

DNA was prepared by lysing cell pellets in 0.1 M Tris-Cl/10 mM EDTA/600 $\mu$g/ml proteinase K at 56° C. for 1 h followed by 95° C. for 15 min. DNA (10 $\mu$l) was used in a 50-$\mu$l PCR containing 12.5 pmol primers, 10 mM Tris-HCl, 50 mM KCl, 0.01% gelatin, 0.1% Triton X-100, 0.1 mM dNTPs, 1 unit Taq polymerase, 3 mM MgCl$_2$ (Promega), and 2.5 $\mu$Ci of [$\alpha$-$^{32}$P]dCTP (Amersham Pharmacia). Primers SK38 and SK39 (18) were used to detect gag. Primers DQ28 and DQ29 amplify cellular HLA-DQ$\alpha$ and were used to quantify total cellular DNA (61). PCR conditions for gag were 1 cycle at 94° C. for 3 min; followed by 28 cycles at 94° C. for 30 s. 60° C. for 30 s, and 72° C. for 30 s; with a final extension cycle at 72° C. for 10 min. At 28 cycles, the PCR had not yet reached saturation as determined in preliminary experiments with different numbers of cycles. Portions (10 $\mu$l) of each PCR were run on an 8% acrylamide gel. Gels were exposed to a Phosphoscreen detector (Molecular Dynamics) and scanned on a STORM PhosphorImager (Molecular Dynamics). Band intensities were measured by using SCANDNASIS (Hitachi Software, Tokyo).

HIV gag Copy Numbers per Subset.

Figure 10A:
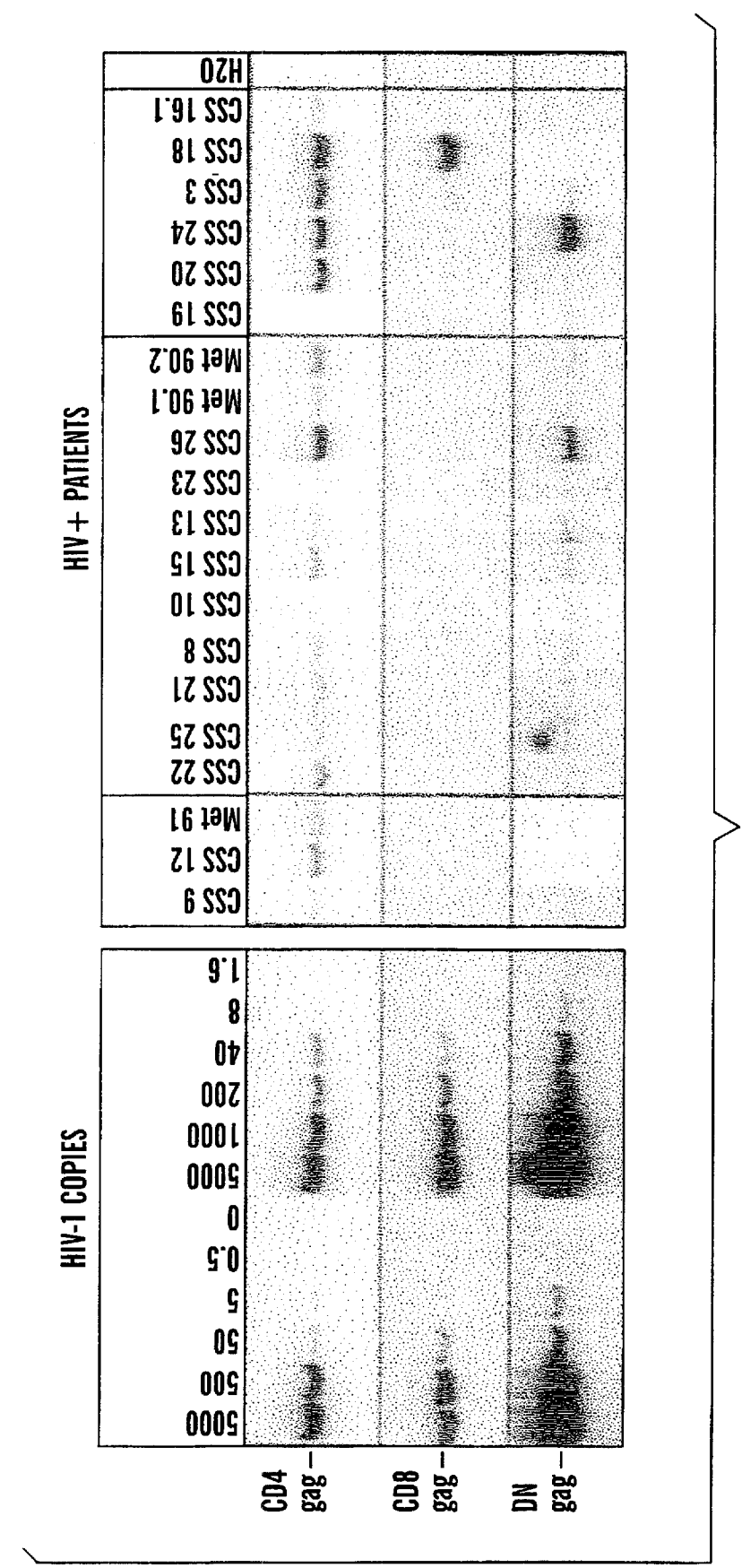
FIG. 10A shows the results from HIV gag DNA PCR in sorted subsets from 19 HIV-infected individuals. Gels were exposed to a Phosphoscreen detector (Molecular Dynamics) and scanned on a PhosphorImager. The controls, labeled HIV-1 copies, represent the indicated cell numbers of ACH-2 cells, containing a single copy of HIV-1 per c II, that were diluted in a constant number of uninfected CEM cells (61). The patient samples are arranged in the same order in Table 2.

A standard linear curve for the HIV gag PCR was obtained by using 10- and 5-fold dilutions of the ACH-2 cell line 20 containing a single copy of the HIV genome. Linear equations of these curves were used to estimate HIV copy numbers for each sample. This estimate was corrected by cell numbers from the FACSvantage counters after sorting. Reproducibility of these estimates is shown for Met90, where similar values were obtained from two separate sorts (FIG. 10B). The correlation between the intensity of PCR bands for cellular DQ DNA and cell counts after sorting (r=0.83) was calculated by using a simple curve fit with CRICKET GRAPH 1.3 (Cricket Software, Malvern, Pa.).

Magnetic Bead Sorting.

PBL were first incubated with a mouse anti-human CD4 antibody (FFB2.3) for 1 h at 4° C. CD4⁺ cells were positively selected with magnetic beads coated with a goat anti-mouse antibody as recommended by the manufacturer (Dynal, Great Neck, N.Y.). The same procedure was repeated sequentially for CD8⁺ and CD3⁺ cells to get the CD3⁺ DN. Note that for some data (see Table 3 and FIG. 12), the CD4 and CD8 antibodies were used simultaneously to isolate a common subset including CD4 single positives, CD8 single positives, and possible CD4/8 double positives (CD4+CD8). The efficacy of the sorts was >95%. The triple-negative (TN) fraction contained B cells, monocytes, and natural killer cells and served as an internal control.

HIV RNA in T Cell Subjects.

RNA was isolated, and cDNA was synthesized (55). CDNA was diluted to obtain substrate cDNA levels corresponding to the indicated cell number equivalents. PCR with primers specific for MS, US, and actin RNA were performed (ref. 7; see Table 3 and FIG. 12).

Coculture Infectivity Assay.

The different fractions of cells complexed with magnetic beads were plated directly with 2×10⁶ to 3×10⁶ phytohemagglutinin-activated blasts (harvested after 2 days) from a noninfected individual and cultured in the presence of IL-2 for 2–4 weeks. Cell-free supernatants were collected every 3–4 days and stored at −20° C. p24 was measured in the supernatants by using an ELISA kit (NEN).

Example 6

Identification of HIV-Infected DN T Cells in vivo

Figure 2:
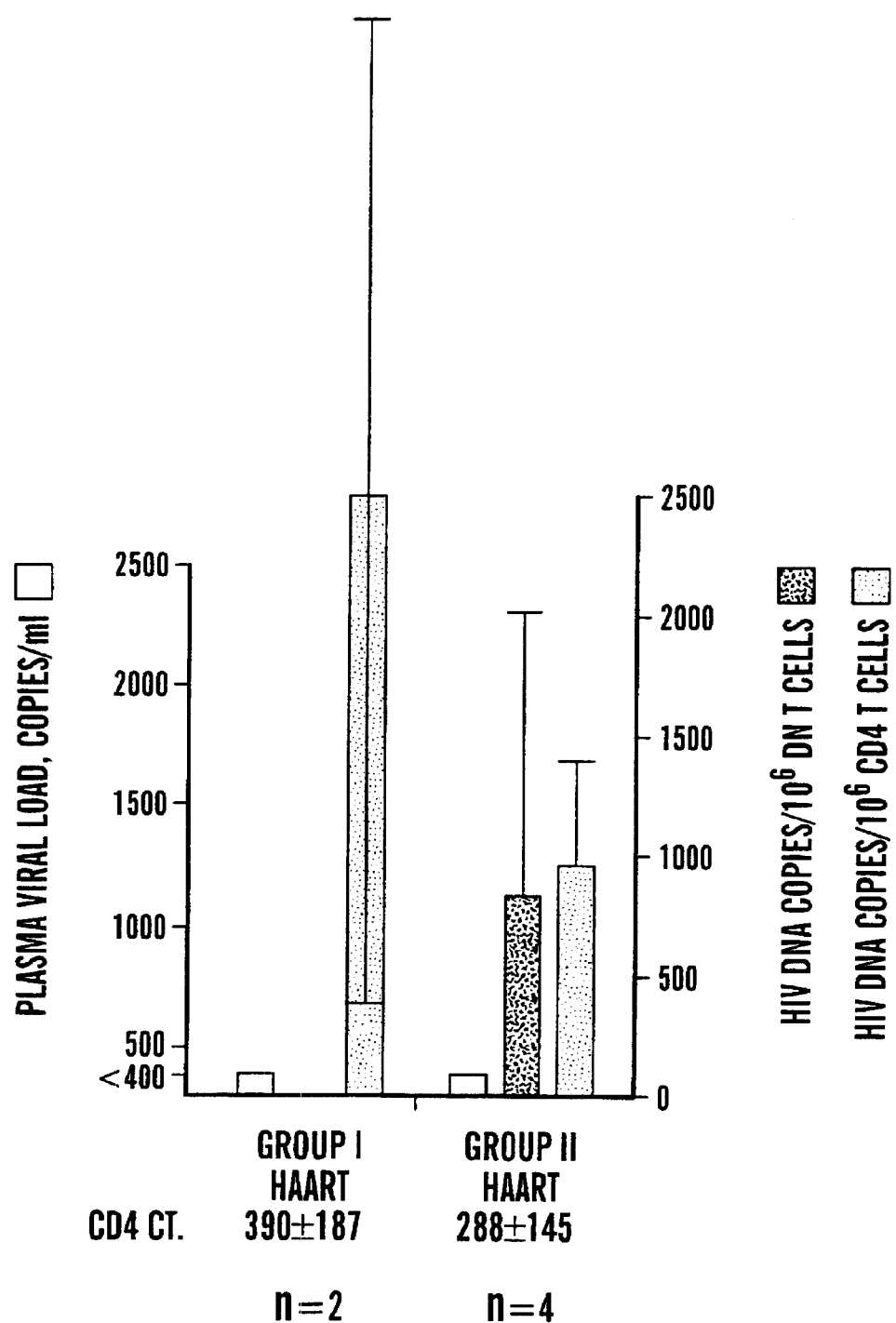
FIG. 2 provides results from patients on cocktail therapy (HAART). All the patients have "no detectable viral load" by the standard Chiron plasma viral load assay. Both groups of patients have detectable viral DNA in the CD4 cells (this is most likely non-viable virus). Group II has detectable viral DNA in the double negative T cells (Possible live replicating virus). Group II has a lower average CD4 count than group 1, e.g. the less complete elimination of HIV seen in group II is associated with persisting damage to the immune system as measured by the total CD4 count.

To test whether HIV-infected DN T cells exist in vivo, peripheral blood T cells from 19 HIV-infected individuals (Table 1) were sorted based on expression of TCR$\alpha\beta$, CD4, and CD8 (FIG. 9). DNA from the sorted subsets was analyzed by PCR (FIG. 2A). HIV gag DNA was detected in CD4⁺ T cells from 94% (17 of 18) of the HIV-positive individuals studied. HIV was found in DN T cells from 84% (16 of 19) of these individuals. The high frequency of HIV detection in DN cells was confirmed by using primers specific for the pol gene of HIV. By contrast, HIV gag was detected in the CD8⁺ fraction in only 31% (16 of 19) of HIV-positive individuals. The number of viral copies per million cells was then estimated (FIG. 10B). The cell number equivalents used for PCR correlated well with PhosphorImager band intensity of HLA-DQ PCR bands, as a measure of consistent PCR efficiency (FIG. 2C). Therefore, cell number data was used to calculate viral loads per $10^6$ cells (FIG. 10B).

The numbers of viral copies were 5,146±6,591 gag copies per $10^6$ cells (mean±SD; range undetectable to 17,937) in the CD4+ subset and 1,603±3,047 gag copies per $10^6$ cells (range undetectable to 10,564) in the DN subset. The highest viral copy numbers in the DN subset were detected in subjects CSS3, CSS13, CSS19, CSS24, and CSS26. Of these patients, four had high plasma viral loads, and one (CSS13) had undetectable plasma viral loads. HIV-positive DN T cells were often present in subjects without detectable plasma load after successful HAART. Among the seven HIV-positive subjects with undetectable plasma viral loads (Table 1), five had HIV DNA in the DN subset, whereas all had HIV DNA in CD4+ and none had HIV DNA in CD8 cells. In most patients, the DNA viral load was higher in CD4 versus DN cells, but in some patients (CSS13, CSS24, and CSS26) the viral loads per $10^6$ cells were about equivalent for CD4 and DN T cells. Considering, on average, 5- to 10-fold greater numbers of CD4 than DN T cells, the viral load in the DN subset represented 10–20% of the total T cell viral DNA in these patients. This leads to the conclusion that a significant number of HIV-infected T cells have a DN phenotype.

The number of viral copies in the CD8+ subset was 589±2,276 gag copies per $10^6$ cells (range undetectable to 10,220). However, data from a single patient (CSS 18) contributed heavily to this average. In contrast to a previous study (59), HIV-infected CD8+ cells were not detected frequently, perhaps because a 28-cycle PCR was used, which is more stringent than the 45-cycle PCR used in the previous study.

Example 7

Analysis of Viral Loads in Patients with or without HAART

Plasma viral loads were correlated with cellular viral loads in CD4 and DN T cells in patients with or without HAART (FIGS. 10D and E). Among patients that were treatment naive or had failed HAART, there was a strict correlation between plasma and cellular viral loads. Among patients with a HAART response (see Table 2), plasma viral loads generally were undetectable, but cellular viral loads were variably present in both CD4 and DN T cells. However, the average CD4 and DN viral loads were decreased by about one log in patients with a HAART response (FIG. 10D and E). Therefore, successful HAART resulted in decreases of both cellular viral loads and plasma viral load. This result implied that HIV-infection in DN T cells was sensitive to antiviral therapy and therefore was likely a productive infection, as opposed to infection with defective virus.

Example 8

Determination of Viral Copy Numbers in Lymph Nodes

Figure 11A:
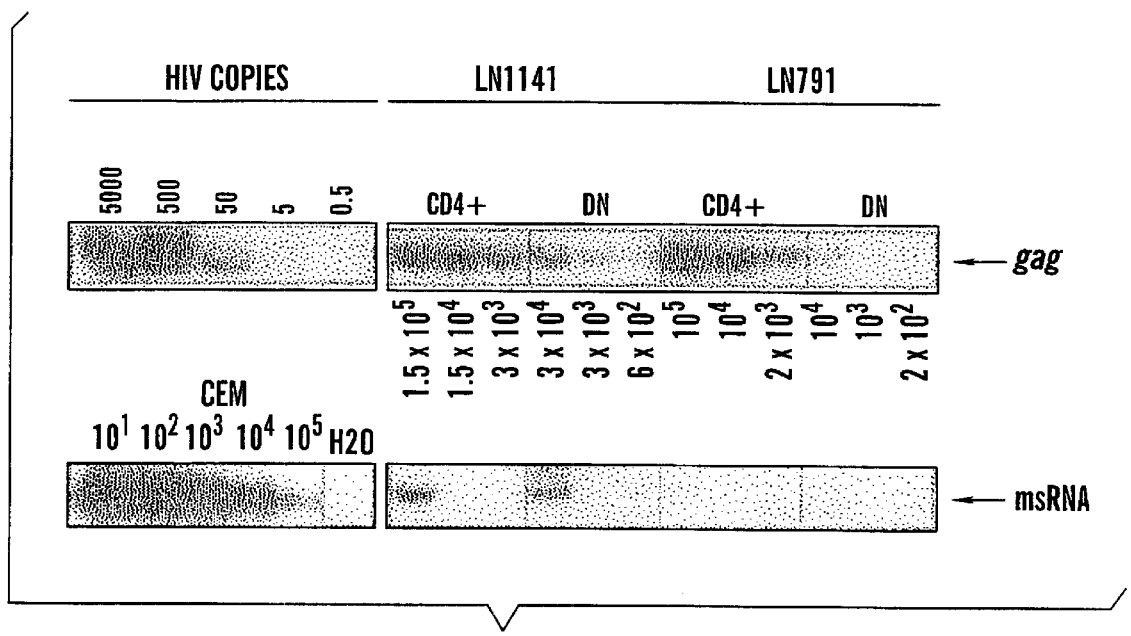
FIG. 11A provides the results from Gag DNA PCR which was performed on isolated CD4 and DN subsets from two LN. ACH-2 cell equivalents were used as an indicator of HIV-1 DNA copy numbers, and PCR substrate DNA from the LN subsets was diluted, as indicated by the cell number equivalents. CDNA templates were used for the MS RNA reverse transcription-PCR (RT-PCR) as described (57). The CEM cell line infected with HIV NL4.3 was used as a control for the specificity of the MS PCR with indicated dilutions starting at approximately $10^5$ cell equivalents for the far left lane.
Figure 11B:
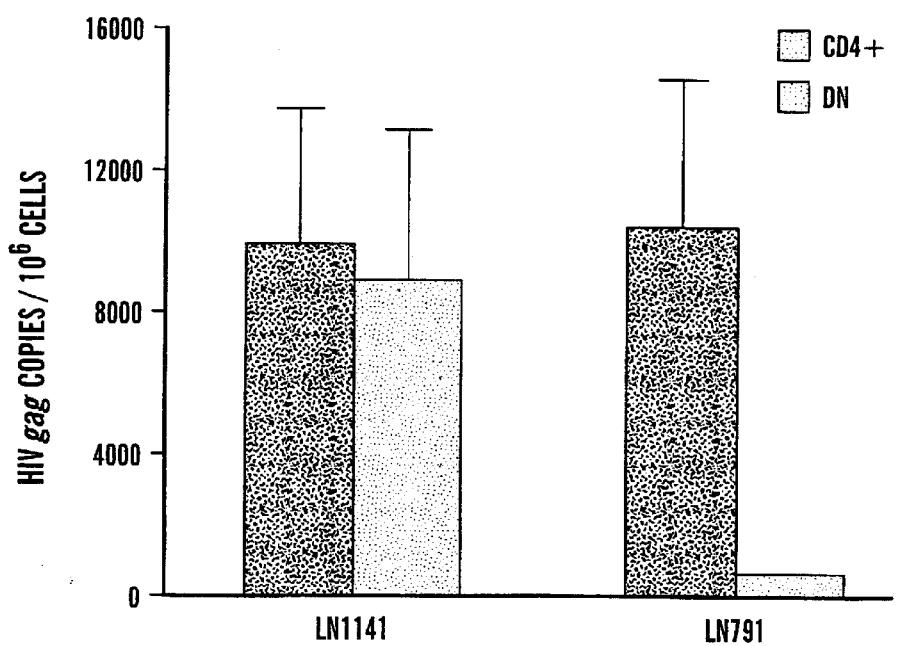
FIG. 11B shows the HIV gag DNA copy numbers per million cells assessed as described for FIG. 10B by extrapolation on to a standard curve obtained from the ACH-2 dilutions. For each subset, three readings were taken by using the band intensities of the three dilutions, and these readings were used to calculate means±SD.

Lymph nodes (LN) are thought to represent a major source of viral production and a site of entrapment of plasma virions (62, 63). Teased LN cells were sorted as described in FIG. 9. HIV gag DNA was detected in CD4+ and in DN T cells from two HIV-infected LN (FIG. 11A). In LN1141, viral copy numbers were similar in CD4+ and DN subsets (FIG. 11B). By contrast, in LN791, HIV DNA was infrequent in DN T cells (FIG. 11B). MS RNA was present in CD4+ and DN T cells from LN1141, indicating productive infection of both subsets. MS RNA was barely detectable in CD4+ and undetectable in DN cells of LN791, indicating lower levels of productive infection in LN791 (FIG. 11A). In this instance, low levels of productive infection correlated with lower levels of HIV gag DNA in the DN subset but had no apparent effect on the levels of HIV gag in the CD4+ subset. Thus, the level of HIV DNA in the DN subsets may perhaps serve as a surrogate indicator of productive infection.

Example 9

Identification of Active HIV in DN Cells

Figure 12:
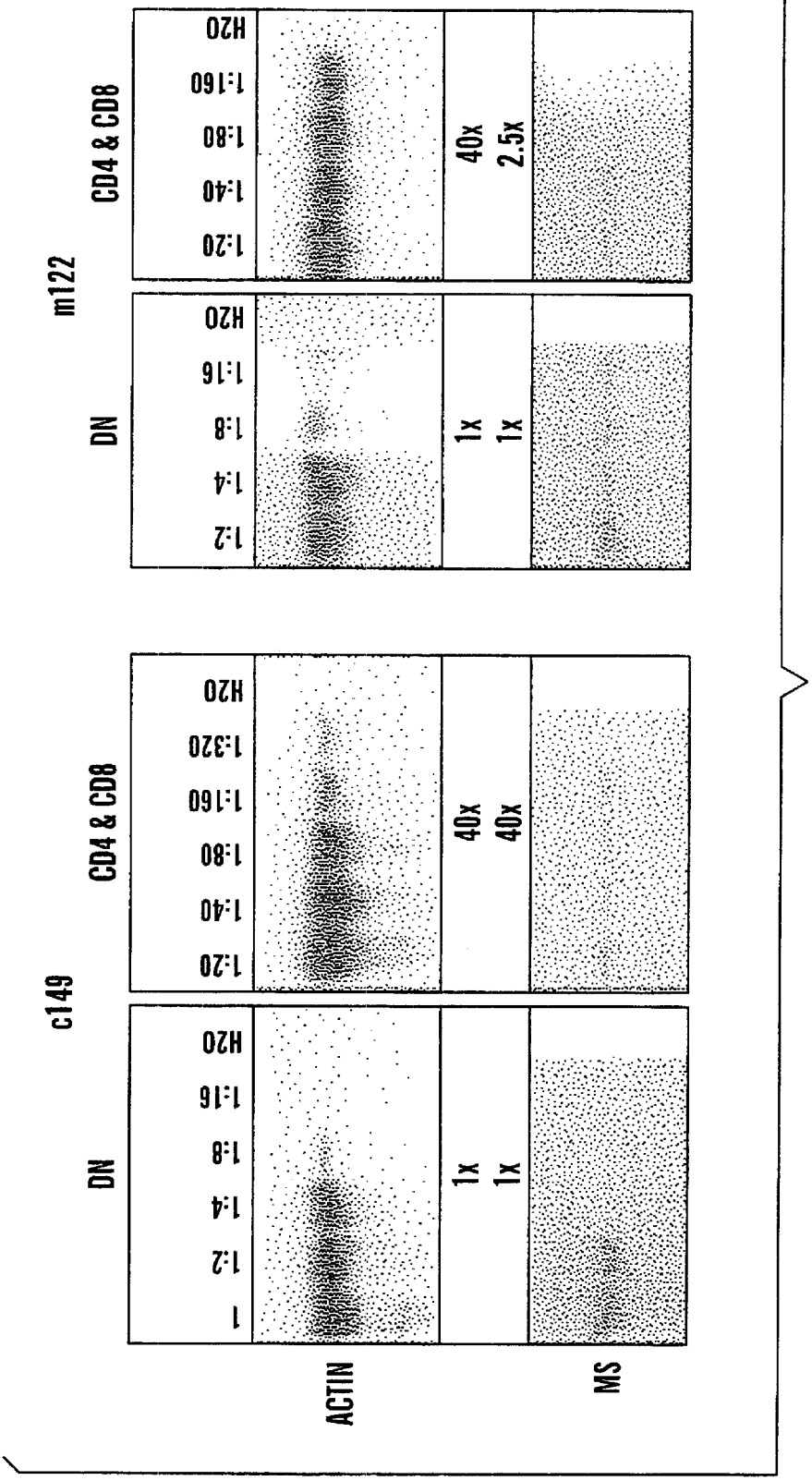
FIG. 12 shows abundant HIV MS RNA in DN subset. DN as well as CD4+CD8 subset isolated by magnetic beads from m122 and c149 were used to extract RNA and synthesize cDNA, which was quantitatively assessed by end-point dilutions and comparisons with cellular actin cDNA. Congruent with the small percentages of DN cells per total CD3+ cells in m122 and c149 (Table 2), actin RT-PCRs indicated an ~40-fold excess of actin message in the CD4+CD8 subset over the DN subset (arbitrarily assigned a 1×value). The ratios for MS RT-PCRs are compared with actin ratios to gauge relative excess of MS RNA in DN versus CD4+CD8 subsets. For c149, the ratio is the same (1:40). indicating , no enrichment of MS RNA in the DN subset; however, for m122, the ratio is 1:2.5 (16:40), representing a 16-fold enrichment of MS RNA in the DN subset.

To test further whether infection of DN T cells was productive, HIV MS RNA, US RNA, and cellular actin RNA were examined in fresh ex vivo PBL samples from 10 HIV-positive subjects (FIG. 12 and Table 3). Because FACS sorting of HIV-infected cells requires paraformaldehyde fixation for biosafety reasons and paraformaldehyde can interfere with RNA isolation, DN as well as the CD4+CD8 subset were isolated with magnetic beads. The cell yields for DN cells were on average 10-fold less than those for CD4+CD8. consistent with percentages of DN cells ranging from 1.9% to 11.3% of total CD3+ cells. As expected, the CD4+CD8 subset contained 10- to 50-fold more RNA than the DN subsets, as assessed by cDNA titrations in an actin RT-PCR. However, RT-PCRs for MS RNA often yielded bands of similar intensity for DN versus CD4+CD8, implying that the DN subset might be enriched for HIV MS RNA. Titrations for he MS RNA PCR (FIG. 12) confirmed this suggestion. For example, the ratio of endpoint dilutions (for the MS PCR, 1:40 or 0.025, and for the actin PCR, 1:40) are equivalent in patient c149. This equivalence suggests equal amounts of MS RNA in DN versus the CD4+CD8 subset when normalized for total cellular RNA. In patient m122, the ratios suggest 16-fold enrichment of MS RNA in the DN subset. This result could be explained by higher percentages of productivity infected cells in the DN subset, by more efficient viral transcription, or by a combination of both. Viral RNAs present in DN cells were not a rare finding. In 5 of 10 patients examined, US and/or MS RNA was detectable in the DN subset (Table 2). When HIV RNA was detectable in DN cells, it was also detectable in the CD4+CD8 subset.

Figure 13:
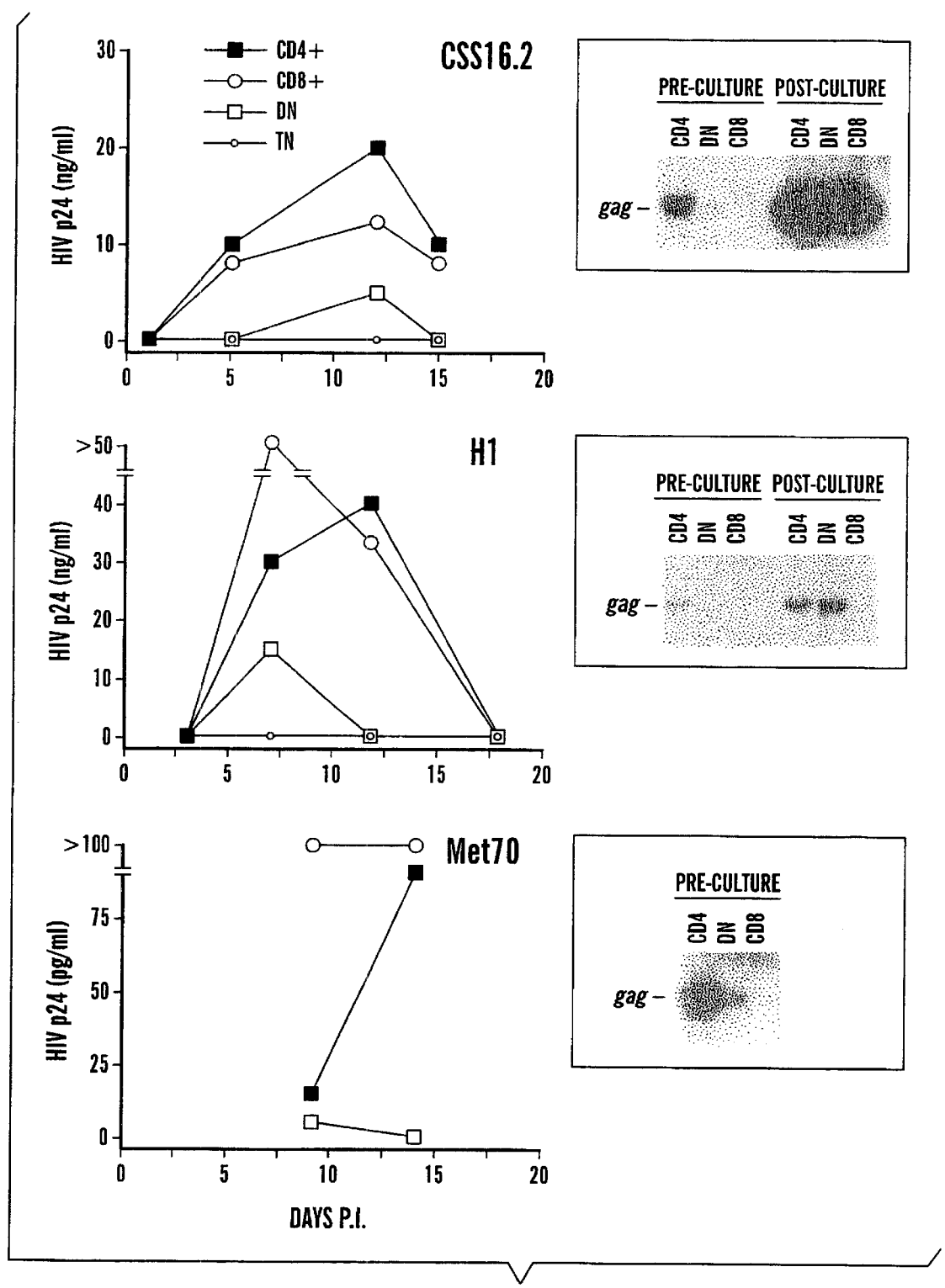
FIG. 13 shows the efficient production of infectious HIV from sorted DN subject. Different fractions of cells from HIV-positive patients were sorted with magnetic beads and cocultured with phytohemagglutinin-activated blasts. Cell-free supernatants were assayed for p24 by using an ELISA. DNA gag PCRs on preculture and postculture sorted subsets are shown.

HIV RNA in DN cells suggests productive HIV infection but does not prove that infectious virus is released. CD4+, CD8+, and CD3+ DN cells were therefore isolated from HIV-positive subjects and cocultured with phytohemagglutinin-activated blasts that serve as indicators or viral transmission. Cell-free supernatants were assayed for p24 by ELISA at various time points as a measure of new HIV production (FIG. 13). HIV p24 was consistently detected from cocultures with CD4+ and DN but not with CD8+ or TN subsets. Virus produced by DN cells from CSS16.2 readily infected the indicator cells, resulting in p24 levels that were even higher than in the parallel culture with CD4+ cells. Note that in patient CSS16, the preculture gag PCR band (FIG. 13 Top Inset) was much weaker for DN that for CD4 cells. For patient H1, HIV infection of the DN subset was not even detectable before culture (FIG. 13 Middle Inset). However, infection of the indicator cells was readily seen when DN T cells of H1 were used as a source of virus. For patient Met70, DN T cells were also able to produce infectious virions, albeit with slower kinetics. In view of the much weaker DNA PCR signal in preculture DN cells versus preculture CD4 cells, DN cells infected with HIV were apparently able to produce infectious virus with greater efficiency. Finally, gag DNA was also measured by PCR in the infected indicator cells at the end of the cocultures (FIG. 13 Insets). HIV DNA was found in all three subsets (CSS16.2) or in CD4+ and DN cells (H1) but not in the TN subset, consistent with the p24 results. Although infectious HIV was rescued from the DN subset of three patients, rescue was not successful in samples from two other patients (CSS8 and Met90.3), both of which had undetectable plasma viral loads.

Down-regulation of CD4 from the cell surface has been well documented in transformed T cell lines infected in the laboratory (64) and in primary lymphocytes infected with a reporter virus (27, 55). If this down-regulation occurs in vivo, one would expect to find HIV-infected DN T cells as described in this study, the first comprehensive analysis of HIV infection in this subset. Although one can neither rule out direct infection of some DN T cells nor exclude that some HIV-positive DN cells derive from infected thymocytes, the simplest explanation for the presence of HIV-positive DN T cells in vivo is CD4 down-regulation occurring after infection of peripheral CD4+ precursors. If HIV-positive DN cells are former CD4+ cells, one would expect continued expression of CD4 mRNA, as previously shown in PBL, infected in vivo with a reporter virus (55). The presence of CD4 mRNA was tested for in CD4, CD8, and DN subsets sorted from HIV-positive patients and found only small amounts of CD4 mRNA in DN cells and in CD8 cells in both HIV-positive and HIV-negative subjects. These results are compatible with a CD4+ origin of HIV infected DN T cells. The absence of high levels of CD4 mRNA in DN cells could be caused by low percentages of HIV-positive cells within the DN subset making it difficult to see increased CD4 mRNA when examining the entire DN subset. The data are also compatible with HIV-positive DN cells derived from other sources, such as thymic DN cells or natural killer T cells with a DN phenotype.

Direct proof for CD4 down-regulation in vivo would require tracking the generation of DN cells from CD4+ precursors. A recent study in monkeys with recombinant simian immunodeficiency virus encoding green fluorescent protein clearly showed that the majority of cells testing positive for green fluorescent protein were CD3+ and that a fraction of them were CD4− (65). Although no quantitative analysis of this subset was made, these results support the data in humans and indicate that the source of HIV-positive DN T cells is most likely infected CD4+ precursors.

The data presented (FIG. 13) suggest that DN T cells were enriched for productive virus compared with CD4+ T cells. Productive infection leads to high cellular levels of viral proteins, and the peptide products of nef env, and vpu have a requisite and cooperative effect on CD4 down-regulation (27). These viral proteins would not be present unless the cell were productively infected. Therefore, cells with down-modulated surface CD4 may represent the fraction of infected cells in which virus is being produced.

Given the redundancy of HIV genes that can mediate CD4 down-regulation, it is likely that this process is important for efficient viral replication. Viral replication in T cells is believed to result directly in cell death and eventual depletion of CD4 T cells (66). However, the paradigm of high CD4 cell turnover and destruction leading to CD4 depletion has been challenged (67) and the importance of T cell production in maintenance of the peripheral pool of naive cells is increasingly recognized (68). Others have noted that apoptosis in ex vivo LN tissues is not correlated with the stage of the disease or viral burden (69) and that it rarely affects productively HIV-infected T cells, affecting instead the surrounding uninfected bystander T cells (70). These results point to indirect mechanisms of cell death that may contribute to overall CD4+ depletion. Of these mechanisms, gp120-induced cell death has been the focus of several studies (53, 71, 72). One possibility is that CD4 down-regulation protects against apoptosis induced by cross-linking of CD4 by gp120. Indeed, in human PBL infected with a reporter virus (55), DN T cells are protected from gp120-induced apoptosis. It is therefore possible that CD4 down-regulation extends the half-life of productively infected T cells in vivo by rendering them less prone to gp120-induced apoptosis.

A major current obstacle in eradicating HIV from patients is the persistence of virus in quiescent T cells despite years of HAART. Quiescent CD4+ T cells have been described as a major "reservoir" of replication-competent virus after initiation of HAART (73–76). These infected cells may have a long half-life in vivo (77) and are thought to be important in continued low-level viral production after initial viremia has abated and also in the reappearance of infectious virus after cessation of HAART. The DN T cells described herein are unlikely to represent quiescent T cells similar to the long-lived reservoir CD4 cells. Rather, they may represent the direct descendants of the quiescent cells, namely those producing infectious HIV. In vitro studies showed that the infected DN cells were observed exclusively after T cell activation and that they had a phenotype of activated memory T cells (55). It seems that the same applies to infected DN cells in vivo.

Infected DN cells can be readily detected in patients on successful HAART in which the plasma viral load is undetectable. These infected DN cells represent evidence of continued HIV production in most patients even after a HAART response. HIV infection is rarely monitored by testing cellular viral loads. The reticence may be related to the presence of much abortive infection in CD4+ cells and therefore "dead" viral DNA. However, infected DN cells may be T cells that by definition contain live virus that is able to produce the viral proteins that down-modulate CD4.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

References

The following references which were cited herein, are hereby incorporated by reference into this application:

1. Ploegh, H. L., *Science,* 280, 248–253 (1998).
2. Trono, D., *Cell;* 82, 189–192 (1995).
3. Schwartz, O. et al., *Nature Med.,* 2, 338–342 (1996).
4. Collins, K. L. et al., *Nature,* 391, 397–401 (1998).
5. Aiken, C. et al., *Cell,* 76, 853–864 (1994).
6. Choremi-Papadopoulou, H. et al., *J Acquir. Imm. Def. Synd.* (1994).
7. Mahalingarn, M. et al., *Clin. Exp. Immunol.,* 102, 481–486 (1995).
8. Zaunders, J. et al., *AIDS,* 9, 561–566 (1995).
9. Puppo, F. et al., *AIDS Res. Hum. Retroviruses,* 13, 1509–1516 (1997).
10. Landay, A.L. et al., *AIDS Res. Hum. Retroviruses,* 14, 445–451 (1998).

11. Gelezunias, R. et al., *FASEB J.*, 8, 593–600 (1994).
12. Stevenson, M. et al., *J. Virol.*, 61, 3741–3748 (1987).
13. Wrightham, M. et al., *Clin. Exp. Immunol.*, 85, 75–79 (1991).
14. Noraz, N. etal., *AIDS Res. Hum. Retroviruses*, 11, 145–154 (1995).
15. He, J. et al., *J. Virol.*, 69, 6705–6711 (1995).
16. Chackerian, B. et al., *J. Virol.*, 71, 3932–3939 (1997).
17. Endres, M. J. et al., *Cell*, 87, 745–756 (1996).
18. Ou, C. Y. et al., *Science*, 239, 295–297 (1988).
19. Saksela, K. et al., *J. Virol.*, 67, 7423–7427 (1993).
20. Bagasra, O. et al., *N. Engl. J. Med.*, 326, 1385–1391 (1992).
21. Landau, N. et al., *Nature*, 334, 159–162 (1988).
22. Wu, L. et al., *J. Exp. Med.*, 185, 1681–1691 (1997).
23. Deng, H. et al., *Nature*, 381, 661–666 (1996).
24. Bleul, C. C. et al., *Proc. Natl. Acad Sci. USA*, 94, 1925–1930 (1997).
25. Larcher, C. et al., *Immunol. Lett.*, 46, 31–36 (1995).
26. Greenberg, M. E. et al., *EMBO J.*, 16, 6964–6976 (1997).
27. Chen, B. et al., *J Virol.*, 70, 6044–6053 (1996).
28. Gowda, S. D. et al., *J. Immunol.*, 142, 773–780 (1989).
29. Zack, J. A. et al., *Cell*, 61, 213–222 (1990).
30. Bukrinsky, M. I. et al., *Science*, 254, 423–427 (1991).
31. Schnittrnan, S. M. et al., *Proc. Natl. Acad. Sci. USA*, 87, 6058–6062 (1990).
32. Spina, C. A. et al., *J. Clin. Invest.*, 99, 1774–1785 (1997).
33. Roederer, M. et al., *J. Clin. Invest.*, 99, 1555–1564 (1997).
34. Cocchi, F. et al., *Science*, 270, 1811–1815 (1995).
35. Kinter, A. L. et al., *Proc. Natl. Acad Sci. USA*, 93, 14076–14081 (1996).
36. Zagury, D. et al., *Proc. Natl. Acad. Sci. USA*, 95, 3857–3861 (1998).
37. Taub, D. D. et al., *J. Immunol.*, 156, 2095–2103 (1996).
38. Chao, C.C. et al., *J. Immunol.*, 159, 1686–1694 (1997).
39. Bennet, T. A. et al., *J. Immunol.*, 156, 3093–3097 (1996).
40. Weeks, B. S. et al., *AIDS Res. Human Retrovir.*, 9, 513–518 (1993).
41. Butcher, E. C. et al., *Science*, 272, 60–66 (1996).
42. Tedder, T. F. et al., *J. Exp. Med.*, 181, 2259–2264 (1995).
43. Xu, J. et al., *J. Exp. Med.*, 183, 589–598 (1996).
44. Schall, T. J. et al., *Nature*, 347, 669–671 (1990).
45. Murphy, W. J. et al., *Eur. J. Immunol.*, 24, 1823–1827 (1994).
46. Murphy, W. J. et al., *J. Immunol.*, 156, 2104–2111 (1996).
47. Wawryk, S. O. et al., *Immunol. Rev.*, 108, 135–161 (1989).
48. Hildreth, J. E. et al., *Science*, 244, 1075–1078 (1989).
49. Luster, A. D. et al., *New Engl. J. Med.*, 338, 436–445 (1998).
50. Veazey, R. S. et al., *Science*, 280, 427–431 (1998).
51. Dalgleish, A. G. et al., *Nature* (London), 312, 763–767 (1984).
52. Klatzmann, D. et al., *Science*, 225, 59–63 (1984).
53. Banda, N. K. et al., *Exp. Med.*, 176, 1099–1106 (1992).
54. Benson, R. E. et al., *Exp. Med.*, 177, 1561–1566 (1993).
55. Marodon, G. et al., *AIDS Res. Hum. Retroviruses*, 15, 161–171 (1999).
56. Yoshimoto, T. et al., *Science*, 270, 1845–1847 (1995).
57. Psallidopoulos, M. C. et al., *J. Virol.*, 63, 4626–4631 (1989).
58. Schnittnan, S. M. et al., *Science*, 245, 305–308 (1989).
59. Flamand, L. et al., *Proc. Natl. Acad. Sci. USA*, 95, 3111–3116 (1998).
60. Livingstone, W. J. et al., *Lancet*, 348, 649–654 (1996).
61. Dobrescu, D. et al., *Proc. Natl. Acad Sci. USA*, 92, 5563–5567 (1995).
62. Pantaleo, G. et al., *Nature* (London), 362, 355–358 (1993).
63. Embreston, J. et al., *Nature* (London), 362, 359–362 (1993).
64. Bour, S. et al., *Microbiol. Rev.*, 59, 63–93 (1995).
65. Alexander, L. et al., *AIDS Res. Hum. Retroviruses*, 15, 11–21 (1999).
66. Gandhi, R. T. et al., *J. Exp. Med*, 187, 1113–1122 (1998).
67. Wolthers, K. C. et al., *Immunol. Today*, 19, 44–48 (1998).
68. Hellerstein, M. et al., *Nat. Med.*, 5, 83–89 (1999).
69. Muro-Cacho, C. A. et al., *J. Immunol*, 154, 5555–5566 (1995).
70. Finkel, T. H. et al., *Nat. Med.*, 1, 129–134 (1995).
71. Nardelli, B. et al., *Proc. Natl. Acad Sci. USA*, 92, 7312–7316 (1995).
72. Cottrez, F. et al., *J. Clin. Invest.*, 99, 257–266 (1997).
73. Finzi, D. et al., *Science*, 278, 1295–1300 (1997).
74. Chun, T. W. et al., *Proc. Natl. Acad Sci. USA*, 94, 13193–13197 (1997).
75. Chun, T. W. et al., *Nature* (London), 387, 183–188 (1997).
76. Wong, J. K. et al., *Science*, 278, 1291–1295 (1997).
77. Ho, D. D., *J. Clin. Invest.*, 99, 2565–2567 (1997).
78. Urdea et al., *Gene* 61, 253–264 (1987).
79. Wahl, G. M. et al., *Methods Enzymol.*, 152, 399–407 (1987).
80. Kimmel, A. R., *Methods Enzymol.*, 152, 507–511 (1987).
81. Dieffenbach et al., PCR Primer, a Laboratory Manual, Cold Spring Harbor Press, Plainview, N.Y. (1995).
82. Hampton, R. et al., Serological Methods, a Laboratory Manual, APS Press, St Paul, Minn., Section IV (1990).
83. Coligan, J. E. et al., Current Protocols in Immunology, Greene Pub. Associates and Wiley-Interscience, New York, N.Y. (1997 and periodic supplements).
84. Maddox, D. E. et al., *J Exp. Med.* 158, 1211–1216 (1983).

What is claimed:

1. A method for determining viral load in a patient infected with human immunodeficiency virus, comprising:

measuring the levels of human immunodeficiency virus in $CD4^-$ $CD8^-$ T cells.

2. The method according to claim 1, further comprising:

isolating T cells;

isolating $CD4^-$ $CD8^-$ cells; and measuring the levels of human immunodeficiency virus in the isolated $CD4^-$ $CD8^-$ T cells.

3. The method according to claim 2, wherein the isolating the T cells comprises:

isolating cells having a T cell specific marker.

4. The method according to claim 3, wherein the T cell specific marker is selected from the group consisting of $CD2^+$, $CD3^+$, and T cell receptor $\alpha\beta$.

5. The method according to claim 4, wherein the T cell specific marker is $CD3^+$.

6. The method according to claim 2, wherein the isolating the T cells is carried out by removing $CD3^+$ T cells using magnetic beads coated with antibodies specific for T cells.

7. The method according to claim 2, wherein the isolating the T cells is carried out by separating T cells using flourescence activated cell sorting.

8. The method according to claim 2, wherein the isolating the T cells is carried out by removing T cells using a panning procedure.

9. The method according to claim 2, wherein the isolating the $CD4^-$ and $CD8^-$ T cells is carried out by removing $CD4^+$ and $CD8^+$ T cells.

10. The method according to claim 9, wherein the isolating the $CD4^-$ and $CD8^-$ T cells is carried using magnetic beads coated with antibodies specific for $CD4^+$ and $CD8^+$ T cells.

11. The method according to claim 9, wherein the isolating the $CD4^-$ and $CD8^-$ T cells is carried out using flourescence activated cell sorting.

12. The method according to claim 9, wherein the isolating the $CD4^-$ and $CD8^-$ T cells is carried out using a panning procedure.

13. The method according to claim 2, wherein the measuring the levels of human immunodeficiency virus is carried out by measuring levels of human immunodeficiency virus DNA, human immunodeficiency virus RNA, or human immunodeficiency virus proteins.

14. The method according to claim 13, wherein the measuring the levels of human immunodeficiency virus is carried out by measuring levels of human immunodeficiency virus DNA.

15. The method according to claim 14, wherein the measuring levels of human immunodeficiency virus DNA is carried out by sequence specific hybridization.

16. The method according to claim 15, wherein sequence specific hybridization utilizes probes specific to a portion of the gag or pol genes.

17. The method according to claim 14, wherein the measuring levels of human immunodeficiency virus DNA further comprises, amplification of the human immunodeficiency virus DNA by polymerase chain reaction.

18. The method according to claim 13, wherein the measuring the levels of human immunodeficiency virus is carried out by measuring levels of human immunodeficiency virus RNA.

19. The method according to claim 18, wherein the measuring levels of human immunodeficiency virus RNA is carried out by sequence specific hybridization.

20. The method according to claim 19, wherein sequence specific hybridization utilizes probes specific to a portion of the gag or pol genes.

21. The method according to claim 18, wherein the measuring levels of human immunodeficiency virus RNA further comprises, amplification of the human immunodeficiency virus RNA by polymerase chain reaction.

22. The method according to claim 18, wherein the human immunodeficiency virus specific transcripts are unspliced viral mRNA transcripts.

23. The method according to claim 18, wherein the human immunodeficiency virus specific transcripts are multispliced viral mRNA transcripts.

24. The method according to claim 13, wherein the measuring the levels of human immunodeficiency virus is carried out by measuring levels of human immunodeficiency virus protein.

25. The method according to claim 24, wherein the measuring levels of human immunodeficiency virus protein comprises:

contacting a sample from the patient with a binding protein which specifically binds to a human immunodeficiency virus protein; and determining the amount of binding protein which binds to the human immunodeficiency virus protein.

26. The method according to claim 25, wherein the binding protein is an antibody.

27. The method according to claim 26, wherein the antibody binds to Nef, Env, or Vpu.

28. The method according to claim 25, wherein the binding protein is a T cell receptor.

29. The method according to claim 28, wherein the T cell receptor is CD4.

30. The method according to claim 1, wherein the patient is being treated with highly active retroviral therapy.

31. The method according to claim 30, wherein the patient has no detectable plasma viral load.

* * * * *

UNITED STATES PATENT AND TRADEMARK OFFICE
CERTIFICATE OF CORRECTION

PATENT NO. : 6,664,042 B1 Page 1 of 1
APPLICATION NO. : 09/890010
DATED : December 16, 2003
INVENTOR(S) : David N. Posnett It is certified that error appears in the above-identified patent and that said Letters Patent is hereby corrected as shown below:

Col. 1 at lines 7-10, delete "The subject matter of this application was made with support from the United States Government under Grant No. ROI AI 22333 from the National Institutes of Health. The United States Government may retain certain rights." and insert --This invention was made with government support under grant ROI AI 22333 awarded by National Institutes of Health. The government has certain rights in the invention-- in its place.

Signed and Sealed this

Seventh Day of April, 2009

JOHN DOLL
*Acting Director of the United States Patent and Trademark Office*